US010350328B2

(12) United States Patent  (10) Patent No.: US 10,350,328 B2
Li et al.  (45) Date of Patent: Jul. 16, 2019

(54) SURFACE MODIFICATION OF MEDICAL OR VETERINARY DEVICES

(71) Applicant: National University of Singapore, Singapore (SG)

(72) Inventors: Min Li, Singapore (SG); Koon Gee Neoh, Singapore (SG); Titus Wai Leong Lau, Singapore (SG); Edmund Chiong, Singapore (SG); En Tang Kang, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 524 days.

(21) Appl. No.: 14/898,646

(22) PCT Filed: Jun. 16, 2014

(86) PCT No.: PCT/SG2014/000283
§ 371 (c)(1),
(2) Date: Dec. 15, 2015

(87) PCT Pub. No.: WO2014/204402
PCT Pub. Date: Dec. 24, 2014

(65) Prior Publication Data
US 2016/0193389 A1    Jul. 7, 2016

(30) Foreign Application Priority Data
Jun. 19, 2013   (GB) .................................. 1310894.9

(51) Int. Cl.
*A61L 27/34*   (2006.01)
*A61L 29/08*   (2006.01)
(Continued)

(52) U.S. Cl.
CPC ................ *A61L 27/34* (2013.01); *A61L 27/28* (2013.01); *A61L 29/043* (2013.01); *A61L 29/049* (2013.01); *A61L 29/085* (2013.01); *A61L 29/16* (2013.01); *B32B 1/02* (2013.01); *B32B 1/08* (2013.01); *C08B 37/0039* (2013.01); *C09D 105/12* (2013.01); *A61L 2420/02* (2013.01); *A61L 2420/06* (2013.01)

(58) Field of Classification Search
CPC ........ A61L 27/28; A61L 27/34; A61L 29/043; A61L 29/049; A61L 29/085; A61L 29/16; B32B 1/02; B32B 1/08
See application file for complete search history.

(56) References Cited

U.S. PATENT DOCUMENTS 5,080,924 A    1/1992  Kamel et al.
5,567,495 A *  10/1996 Modak .................... A61L 29/16
                                                         428/36.9
(Continued)

FOREIGN PATENT DOCUMENTS

WO    97/46590 A1    12/1997
WO    02/060505 A2    8/2002
WO    2003072155 A1   9/2003

OTHER PUBLICATIONS

D.W. Hutmacher, et al., An Introduction to Biodegradable Materials for Tissue Engineering Applications. Annals Academy of Medicine Singapore, Mar. 2001 vol. 30 No. 2; pp. 183-191.

(Continued)

*Primary Examiner* — Walter Aughenbaugh
(74) *Attorney, Agent, or Firm* — King & Schickli, PLLC

(57) ABSTRACT

The invention concerns a medical or veterinary device comprising a covalently immobilized and cross-linked agarose coating, a method for the production of same and a cross-linked agarose coating.

19 Claims, 20 Drawing Sheets

(51) Int. Cl.
*B32B 1/08* (2006.01)
*A61L 27/28* (2006.01)
*B32B 1/02* (2006.01)
*A61L 29/04* (2006.01)
*A61L 29/16* (2006.01)
*C08B 37/00* (2006.01)
*C09D 105/12* (2006.01)

(56) References Cited

U.S. PATENT DOCUMENTS

| 5,843,089 | A | | 12/1998 | Sahatjian et al. |
| 6,635,269 | B1 | * | 10/2003 | Jennissen ................ A61L 27/28 |
| | | | | 424/423 |
| 2005/0249724 | A1 | * | 11/2005 | Lihme ................ B01D 15/3804 |
| | | | | 424/140.1 |
| 2015/0065951 | A1 | * | 3/2015 | Freyman .......... A61B 17/12186 |
| | | | | 604/82 |

OTHER PUBLICATIONS

J.M. Guisan, Aldehyde-Agarose Gels as Activated Supports for Immobilization-Stabilization of Enzymes. Enzyme Microb. Technol., 1988, vol. 10, June, pp. 375-382.
Written Opinion of the International Search Authority dated Aug. 13, 2014.

* cited by examiner

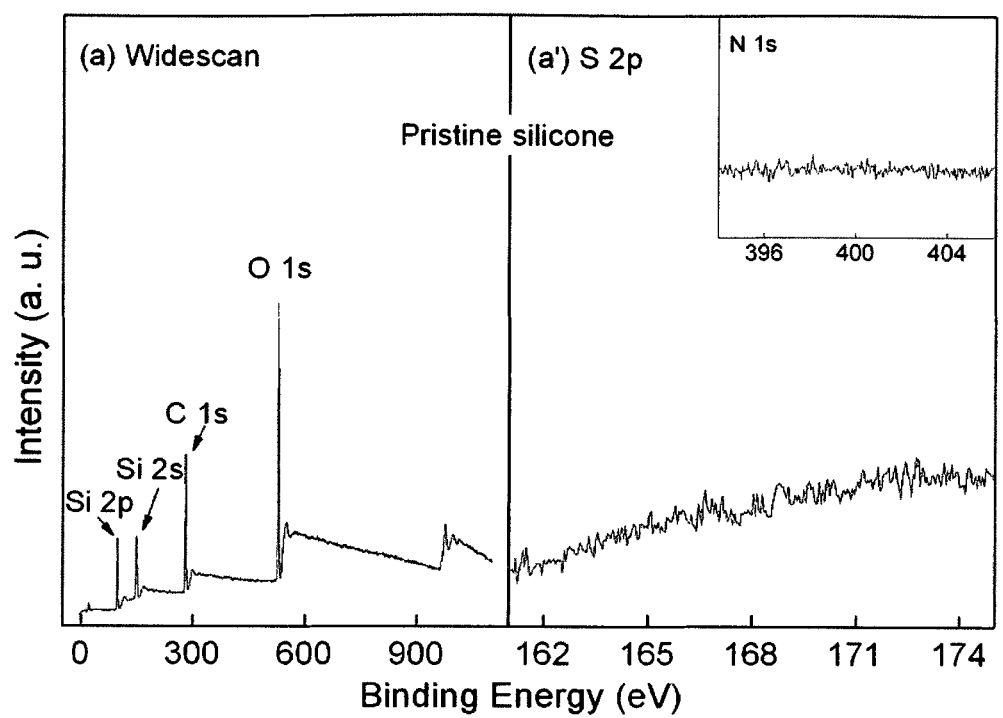
Figure S1

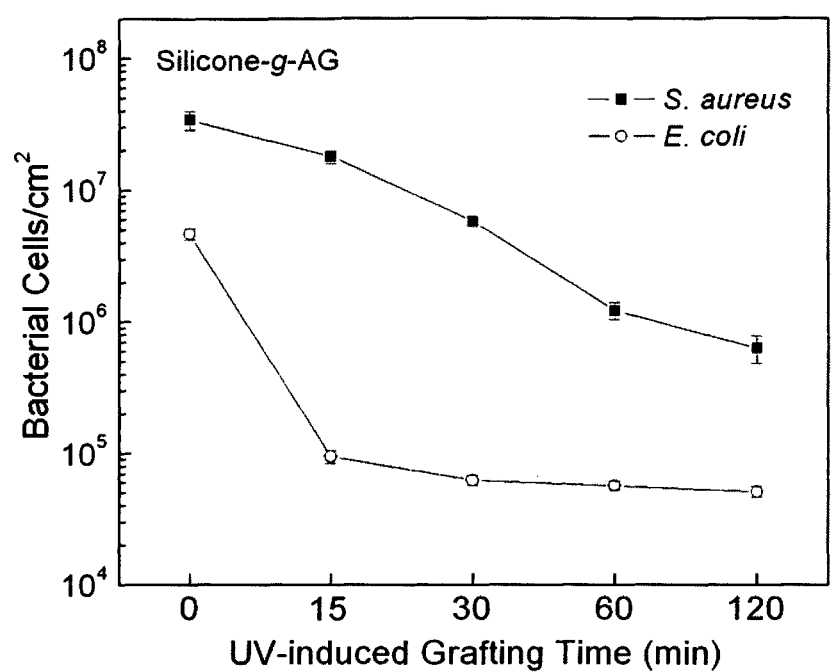
Figure S2

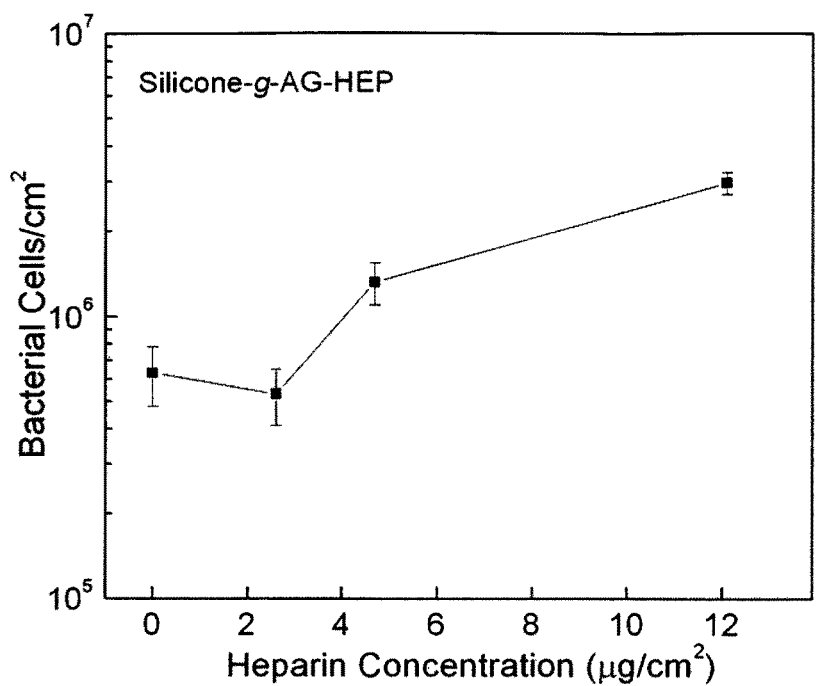
Figure S3
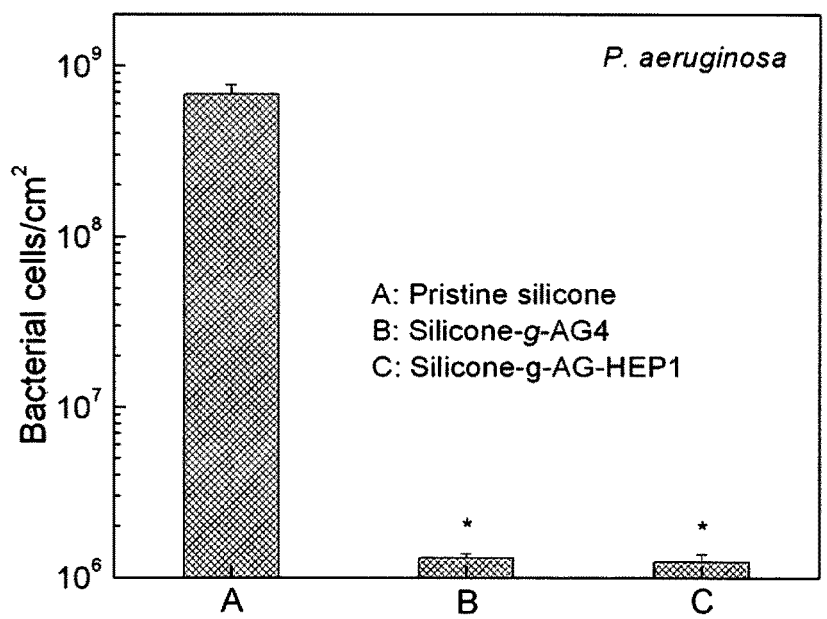
Figure S4

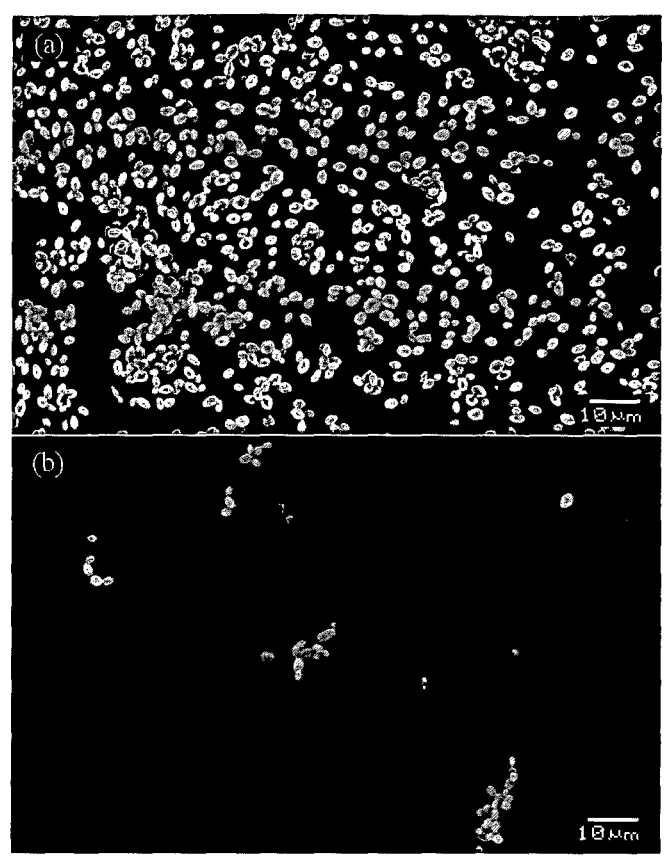
Figure S5

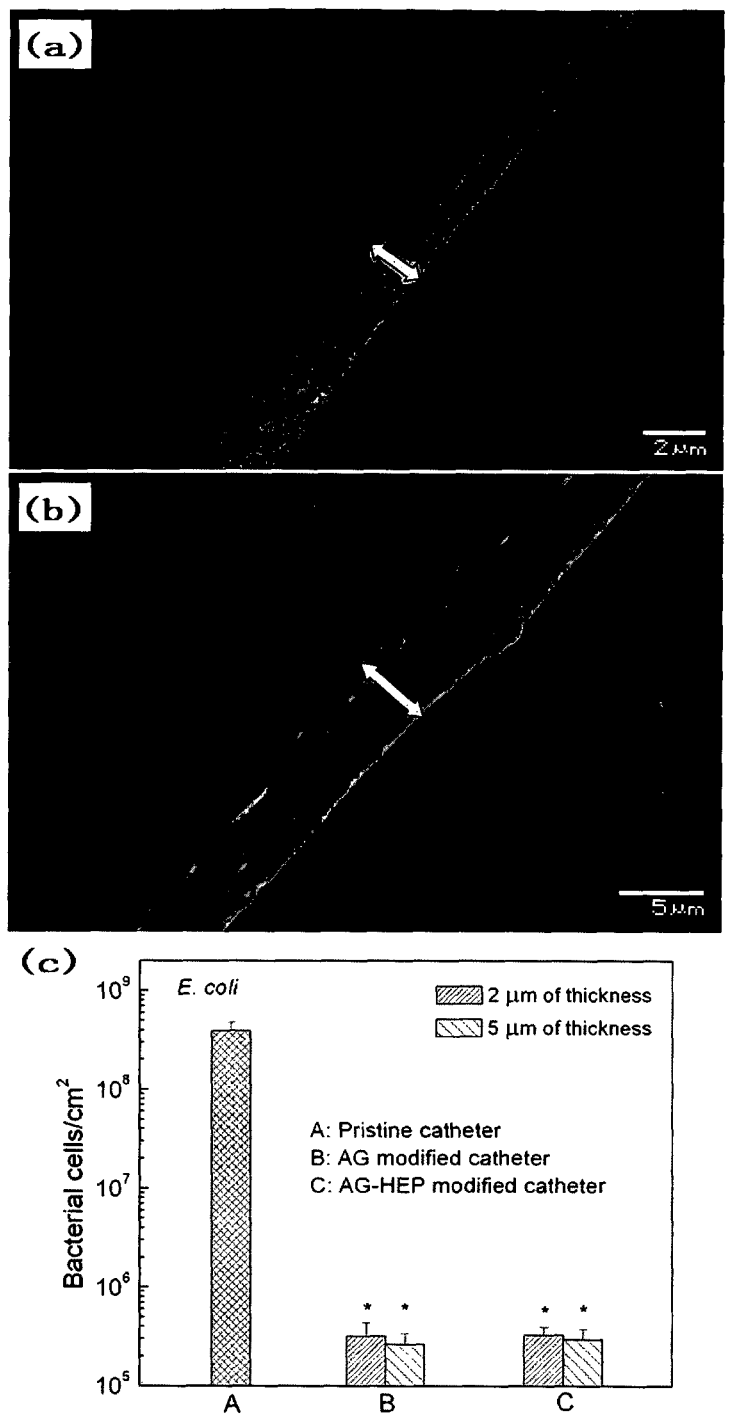
Figure S6

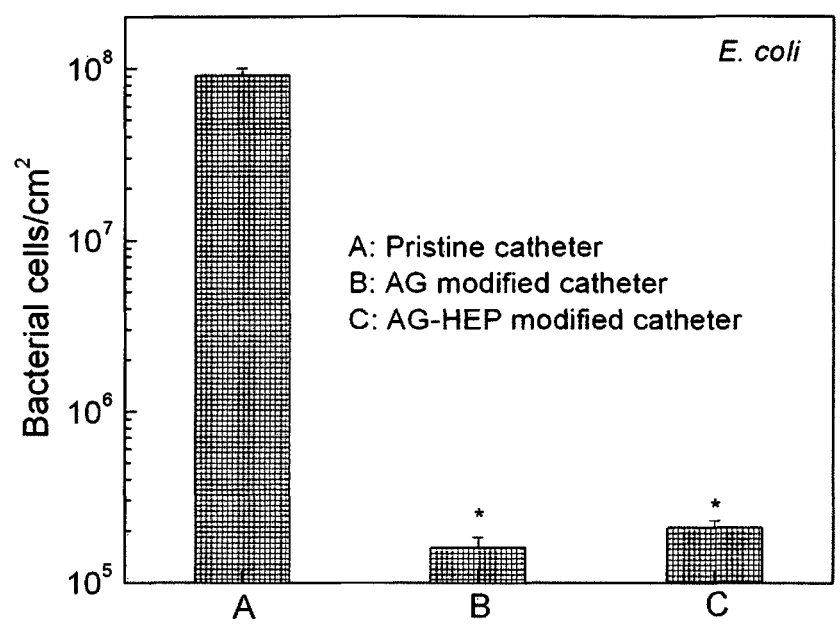
Figure S7

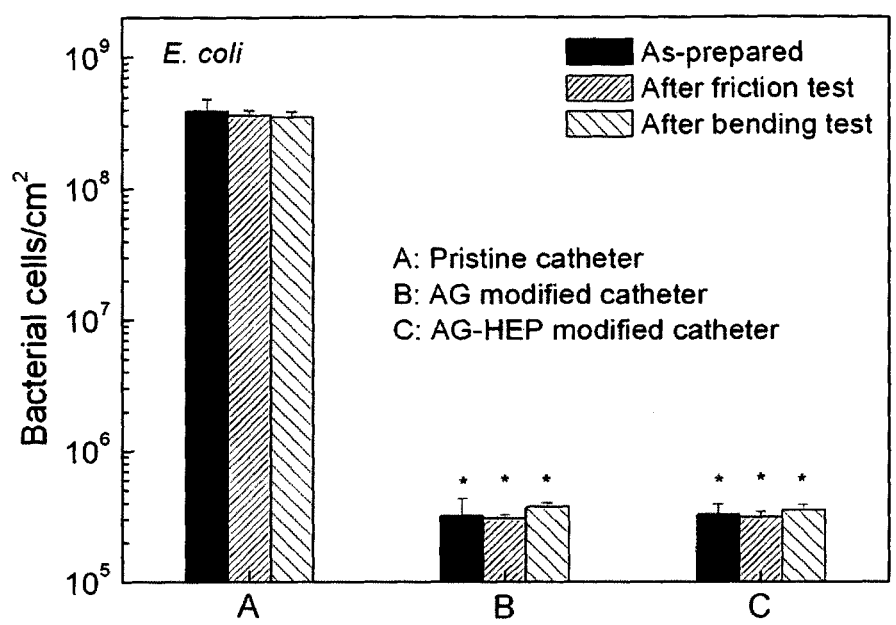
Figure S8

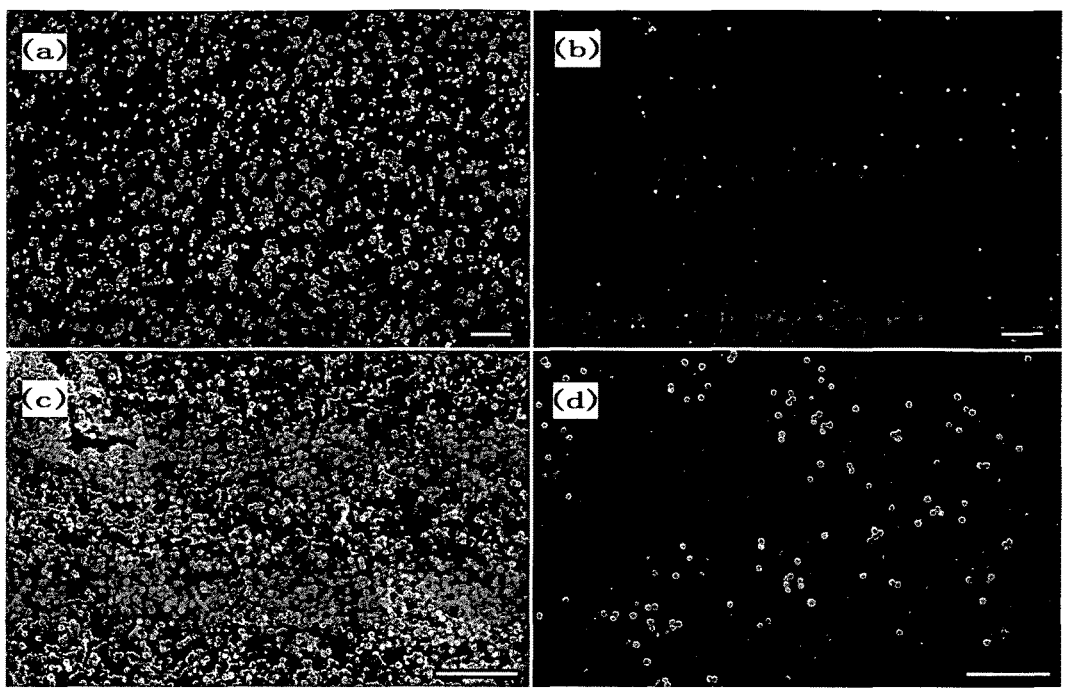
Figure S9

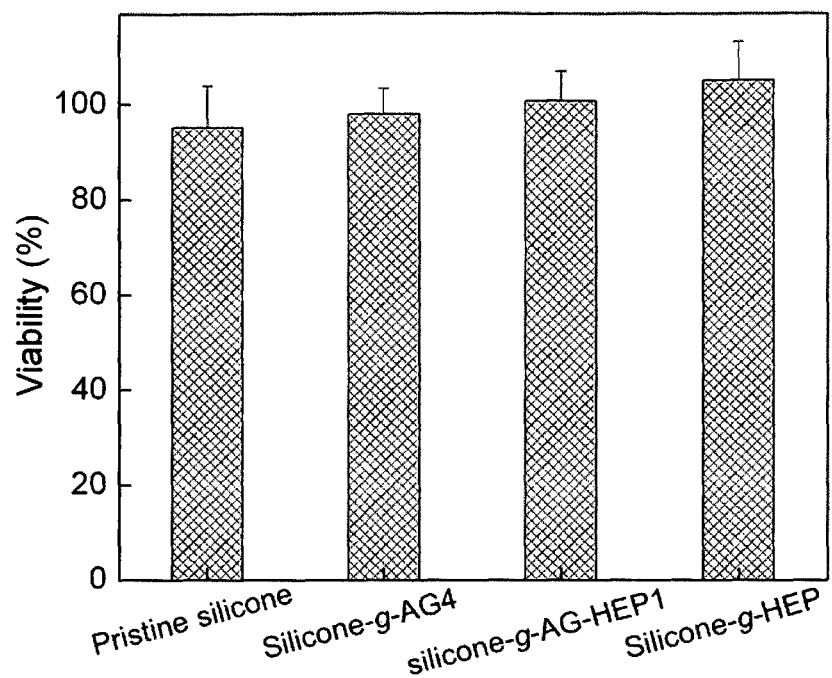
Figure S10
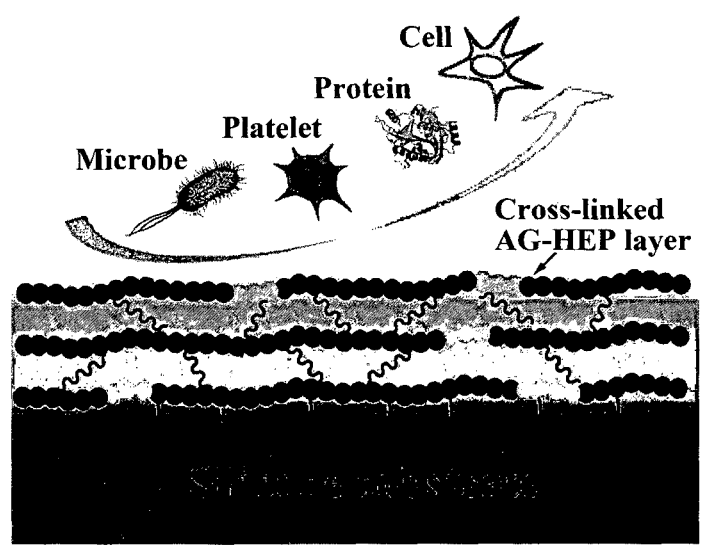
Figure S11

SURFACE MODIFICATION OF MEDICAL OR VETERINARY DEVICES

This application is the national stage of international patent application no. PCT/SG2014/000283 filed on Jun. 16, 2014 which in turn claims priority from British Patent Application Ser. No. 1310894.9 filed on Jun. 19, 2013, the disclosures of each of which are incorporated herein by reference in their entirety.

TECHNICAL FIELD

The invention concerns a medical or veterinary device comprising a covalently immobilized and cross-linked agarose coating, a method for the production of same and a cross-linked agarose coating.

BACKGROUND

Peritoneal dialysis (PD) is an effective home-based dialysis treatment modality for patients with severe renal disease, and it has been used in many countries as a significantly lower cost alternative to hemodialysis. However, the success of PD may be compromised by complications related to the catheter, which is usually made of silicone. Biofouling (in the form of protein adsorption and cell adhesion) and microbial (bacterial and fungal) attachment on the highly hydrophobic silicone surface may result in omental wrapping and infection, which is the leading cause of PD outflow failure and the second most common cause of death for PD patients, respectively. In addition, when in contact with blood, platelet adhesion and activation-induced thrombosis may lead to intraluminal obstruction of PD catheters. The PD catheter can be considered the "lifeline" of the PD patient, and catheter-related complications are the primary obstacle to the widespread use of PD. Since the introduction of a Tenckhoff catheter in mid-1960s, the development of new PD catheter designs has not shown convincing improvement in reducing infection and increasing the survival rates of PD patients.[1] Thus, in recent years, modification of the catheter surface to improve its antifouling, antibacterial and hemocompatible properties has attracted increasing interest.[2]

Another type of catheter, the central venous catheter (commonly made of polyurethane or silicone), is widely used clinically for administering medication, withdrawal of blood samples and hemodialysis treatment. Microbial colonization can occur readily either on the inside or outside of these indwelling catheters, and catheter-associated bloodstream infections (CABSIs) resulting from use of such vascular access devices remain a major clinical problem with adverse effects on patient morbidity, mortality, and healthcare cost. A similar situation arises from the use of indwelling urinary catheters (usually made of silicone), which are standard medical devices in hospital and nursing home settings. Catheter-associated urinary tract infections (CAUTIs) are the commonest hospital-acquired infection worldwide. Thus, surface modification of catheters to inhibit microbial colonization would be highly beneficial in combating CABSIs and CAUTIs.

Tethering of functional polymer coatings via covalent bonding provides an effective way to modify catheter surface properties. The synthetic hydrophilic polymer, poly (ethylene glycol) (PEG), and its derivatives are the most widely used antifouling and antibacterial materials. However, PEG suffers from some limitations: PEG-coated surfaces are unable to reduce protein adsorption to very low levels due to their interactions with proteins, and they are also susceptible to oxidative degradation in the presence of oxygen and transitional metal ions which limits their long-term antifouling and antibacterial performance in vivo. Other synthetic polymers such as poly(acrylamide)s, poly (sulfobetaine methacrylate),[3,4] poly(carboxybetaine methacrylate) and poly(peptoid)s have been extensively investigated for use as antifouling coatings. Natural polymers, as compared with their synthetic counterparts derived from petrochemicals, provide an attractive alternative. Chitosan and its derivatives are the most widely used natural polymers for antibacterial coatings, but their antifouling properties are limited because of their strong interactions with proteins.[5] Heparin (HEP), a commonly-used anticoagulant agent, has been reported to provide an antibacterial coating which can reduce infection both in vitro and in vivo.[6] However, the antibacterial effect of HEP is still debatable. Some studies report that HEP does not significantly reduce biofilm formation by $S.$ $aureus$ and may even stimulate the process.[7,8] Further, immobilization of protein-degrading enzymes, such as pronase and α-chymotrypsin, has been found to reduce protein adsorption on surfaces.[9,10]

Agarose (AG) is a neutral polysaccharide, which is derived from agar. As a U. S. Food and Drug Administration (FDA) approved ingredient, AG is widely used in many fields of biomedical applications, such as nerve regeneration, drug and gene delivery, and dental impression due to its biocompatibility, stability and inertness. In earlier reports, AG, in the form of a film and hydrogel, was shown to resist $Proteus$ $mirabilis$ bacterial adhesion[11] and marine fouling.[12]

At present, surface modification of biomaterials such as silicone, polyurethane and titanium with covalently immobilized natural polymer coatings for the long-term improvement of its antifouling, antibacterial/antifungal and hemocompatible properties is lacking.

SUMMARY

According to a first aspect of the invention there is provided a medical or veterinary device comprising, on at least a part of its surface, a covalently immobilized and cross-linked agarose coating.

In a preferred embodiment of the invention said coating is provided on a biomaterial surface such as silicone, polyurethane or titanium surface, ideally a medical grade biomaterial surface.

A problem frequently encountered in biomaterial surface modification, other than in metallic surfaces, is hydrophobic recovery, which is caused by the re-orientation and migration of the hydrophobic biomaterial segments and the coating polymer, due to the high flexibility and low glass transition temperature of the biomaterial polymer.

Thus, reference herein to an immobilized and cross-linked coating is to a coating that prevents hydrophobic recovery of polymeric materials and/or is stable or has improved stability with respect to existing coatings. Thus, the agarose coating in this work was crosslinked to prevent hydrophobic recovery and improve its stability.

More preferably, said coating is provided on at least a part of the device that makes contact with a patient.

In yet a further preferred embodiment of the invention modification of agarose by the introduction of acrylate, methacrylate, (meth)acrylamide, silane, thiol, azide, alkyne, vinylpyridine or vinylimidazole groups, or derivatives of these groups such as, without limitation, acrylic anhydride, methacrylic chloride, N-hydroxyethyl (meth)acrylamide, 1-2-carboxyethyl-4-vinylpyridinium bromide, and 1-hydroxyethyl-3-vinylimidazolium bromide as well as others known to those skilled in the art, was carried out to facilitate covalent immobilization and crosslinking of the agarose coating. Thus modified agarose such as, in one embodiment, acrylated agarose was used for the coating.

Additionally, or alternatively, said coating also comprises heparin and ideally modified heparin. Most preferably, heparin is modified with methacrylate, acrylate, (meth)acrylamide, silane, thiol, azide, alkyne, vinylpyridine or vinylimidazole groups, or derivatives of these groups such as, without limitation, acrylic anhydride, methacrylic chloride, N-hydroxyethyl (meth)acrylamide, 1-2-carboxyethyl-4-vinylpyridinium bromide, and 1-hydroxyethyl-3-vinylimidazolium bromide as well as others known those skilled in the art, so as to be covalently incorporated into the cross-linked AG coating.

Thus, ideally, HEP modified with acrylate groups, such as methacrylate groups, was covalently incorporated into the crosslinked AG layer to further improve the device's haemocompatibility.

More preferably still, said coating is 1-10 μm thick and most preferably 2, 3, 4, or 5 μm thick, as demonstrated herein a coating of 2 μm is effective at achieving the desired biological properties and so the coating is ideally 2 μm or thereabouts.

Yet more preferably, the amount of heparin in the cross-linked agarose coating is 1-15 μg/cm$^2$ and, most ideally, 1, 2, 3, 4, or 5 μg/cm$^2$, yet more ideally 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8 or 2.9 μg/cm$^2$ and more preferably 2.6 μg/cm$^2$. We have discovered that if the immobilized heparin is at or about 2.6 μg/cm$^2$ the protein-repellent property of the coating, and in particular the agarose component, is preserved. Moreover, if the surface concentration of immobilized heparin is restricted to at or about 2.6 μg/cm$^2$ or less, the antibacterial efficacy of agarose and heparin will not be significantly different from that of agarose alone.

We have found that agarose, and also ideally heparin, when covalently immobilized on a medical grade biomaterial surface such as a silicone surface provided on, such as, without limitation, a catheter surface, e.g. urinary catheter, peritoneal dialysis catheter or central venous catheter, has/have improved antibacterial, antifungal, antifouling and hemocompatible properties. Surprisingly, we have discovered that the adhesion and biofilm formation of both Gram-negative and Gram-positive bacteria were reduced by 98% and >99%, respectively, on an agarose-modified surface according to the invention when compared to that on pristine silicone. These results were obtained regardless of whether the underlying surface was made from silicone, polyurethane or titanium. The agarose-modified surface also inhibited the development of fungal biofilm. A cross-linked agarose coating of 1, 2, 3, 4 or 5 μm thickness is preferred, more ideally a coating of ~2 μm thickness is preferred because it is stable and maintains its antimicrobial efficacy after 30 days aging in lysozyme solution and also after autoclaving. Moreover, we have discovered that the cross-linked agarose coating can effectively resist non-specific protein adsorption and fibroblast and platelet adhesion. Advantageously, co-immobilization of ~2.6 μg/cm$^2$ of heparin in the coating further improves hemocompatibility by inhibiting platelet activation, prolonging plasma recalcification time (PRT) and reducing the degree of hemolysis, whilst retaining the antifouling efficacy of the coating.

According to a second aspect of the invention there is provided a method for manufacturing a medical or veterinary device having, on at least a part of its surface, a covalently immobilized and cross-linked agarose coating comprising:

i. oxidising a surface of said device;
ii. exposing said oxidized surface to modified agarose; and
iii. curing said surface.

In a preferred method of the invention said agarose is modified by the addition of acrylate, methacrylate, (meth)acrylamide, silane, thiol, azide, alkyne, vinylpyridine or vinylimidazole groups, or derivatives of these groups well known to those skilled in the art.

In yet a further preferred method of the invention oxidising said surface involves either exposing said surface to oxygen plasma or ozone. Alternatively, or additionally, said surface is oxidised using plasma treatment with gases such as argon, hydrogen, nitrogen or ammonia followed by exposure to air. Yet again, said surface may be oxidized using corona discharge treatment or gamma irradiation.

In yet a further preferred method of the invention exposing said oxidized surface to modified agarose involves the use of an aqueous solution such as acrylated-agarose aqueous solution, typically but not exclusively at 5 wt. %, and ideally also coating this solution onto the surface of the biomaterial, ideally using a spin-coating procedure or via immersion of the biomaterial in the solution.

In yet a further preferred method of the invention said curing is undertaken using either Ultra violet (UV) light or heat. Ideally, curing is undertaken in a degassed environment. In the instance where UV is used to cure the surface the amount of UV determines the amount of curing and we have found that with increasing UV irradiation time (e.g. from 15 min to 120 min) increases in the grafting density of the immobilized agarose.

In yet a further preferred method of the invention said oxidised surface is also exposed to modified heparin. Ideally a mixture of acrylated agarose and methacrylated heparin solutions are used. Preferably, the concentration of acrylated AG and/or methacrylated HEP in the solutions was between 1-5 wt %, ideally, 5 wt. %.

Preferably the amount of methacrylated heparin in the coating is ~2.6 μg/cm$^2$. According to a further aspect of the invention there is provided a catheter having, on at least a part of its surface, a covalently immobilized and cross-linked agarose coating.

According to a further aspect of the invention there is provided a catheter having, on at least a part of its surface, a covalently immobilized and cross-linked agarose and heparin coating.

In this aspect of the invention said concentration of heparin is ~2.6 μg/cm$^2$.

In any of the afore aspects said catheter is a peritoneal dialysis catheter or a central venous catheter or a urinary catheter.

According to a further aspect of the invention there is provided a medical or veterinary device adapted for preventing a bacterial or fungal infection comprising a medical device which has on at least a part of its surface a covalently immobilized and cross-linked agarose coating as described herein.

According to yet a further aspect of the invention there is provided a medical or veterinary device adapted for preventing omental wrapping comprising a medical device which has on at least a part of its surface a covalently immobilized and cross-linked agarose coating as described herein.

According to yet a further aspect of the invention there is provided a cross-linked agarose coating as described herein for applying in a covalently immobilized manner to at least a part of a surface of a medical or veterinary device for preventing biofouling, a bacterial or fungal infection.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Unless specifically stated or obvious from context, as used herein, the term "about" is understood as "approximately or nearly" and within a range of normal tolerance in the art, for example within 2 standard deviations of the mean. "About" can be understood as plus or minus 10% of the numerical value of a number with which it is being used. Unless otherwise clear from the context, all numerical values provided herein are modified by the term "about".

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the description and claims of this specification agarose is denoted as AG and heparin as HEP.

BRIEF DESCRIPTION OF THE DRAWINGS

An embodiment of the present invention will now be described by way of example only with particular reference to the following wherein:
Main Figures FIG. 1 Schematic illustration of the modification of silicone surface via oxygen plasma or ozone treatment for generating peroxides and hydroxyl peroxides on the silicone surface to serve as anchor sites for the subsequent immobilization of the AG polymer chains (Step (1)), and UV or heat-induced immobilization and crosslinking of acrylated AG and methacrylated HEP (Step (2)).

Figure 1:
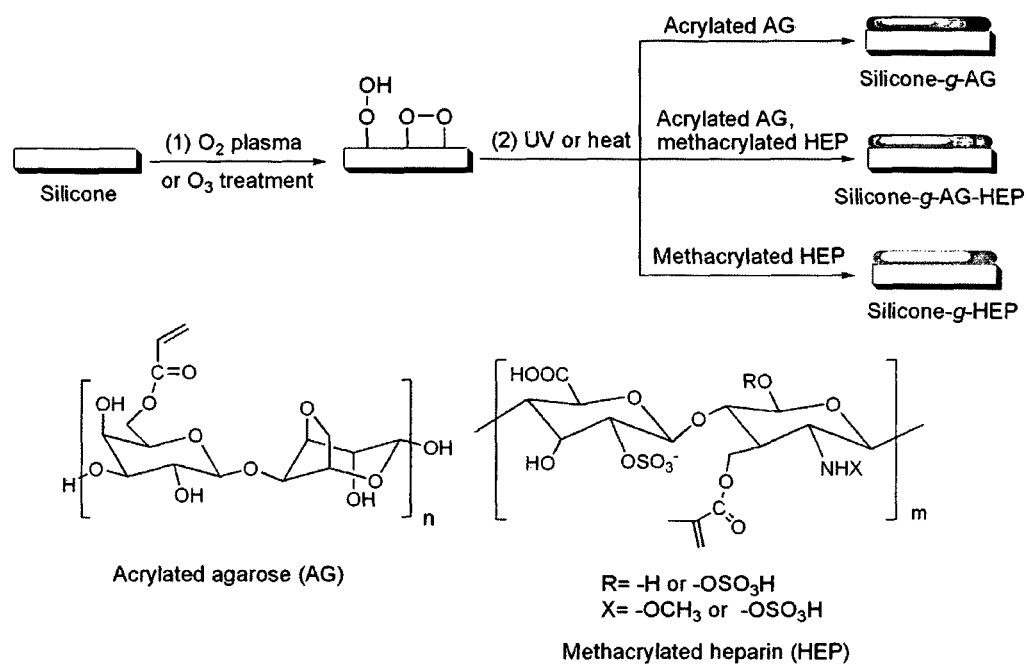

FIG. S2 Effect of UV-induced grafting time on the number of adherent $S.$ $aureus$ and $E.$ $coli$ cells on the Silicone-g-AG films. The number of adherent $S.$ $aureus$ and $E.$ $coli$ cells on the film surface after exposure to a PBS suspension of the respective bacterium ($10^8$ cells/mL) for 4 h was quantified using the spread plate method.

FIG. S3 Effect of concentration of immobilized heparin on the number of adherent $S.$ $aureus$ cells on the Silicone-g-AG-HEP films. The number of adherent $S.$ $aureus$ cells on the film surface after exposure to a PBS suspension of *S. aureus* ($10^8$ cells/mL) for 4 h was quantified using the spread plate method.

FIG. S4 Quantitative count of adherent *P. aeruginosa* cells per $cm^2$ of the pristine silicone surface and agarose modified (with and without heparin) film surface after incubation in growth medium containing $10^7$ bacterial cells/mL for 48 h as determined by the spread plate method. * Significant differences (P<0.05) compared with pristine silicone.

FIG. S5 SEM images of *C. glabrata* biofilm on (a) pristine silicone and (b) Silicone-g-AG4 films after incubation in growth medium containing $10^7$ fungal cells/mL for 24 h. Scale bar is 10 μm.

FIG. S6 SEM images of the cross-section of AG grafted PD catheter segment prepared with a heating period of (a) 8 h and (b) 18 h. Scale bar in (a) and (b) is 2 and 5 μm, respectively. (c) Quantitative count of adherent *E. coli* cells per $cm^2$ of the pristine and modified PD catheter segment surface after incubation in growth medium containing $10^7$ bacterial cells/mL for 48 h as determined by the spread plate method. * Significant differences (P<0.05) compared with pristine PD catheter.

FIG. S7 Quantitative count of adherent *E. coli* cells per $cm^2$ of the pristine and modified urinary catheter segment surface after incubation in growth medium containing $10^7$ bacterial cells/mL for 48 h as determined by the spread plate method. * Significant differences (P<0.05) compared with pristine urinary catheter.

FIG. S8 Quantitative count of adherent *E. coli* cells per $cm^2$ of the pristine and modified PD catheter segment surface after incubation in growth medium containing $10^7$ bacterial cells/mL for 48 h as determined by the spread plate method. * Significant differences (P<0.05) compared with pristine PD catheter.

FIG. S9 SEM images of (a,b) *S. aureus* adhesion and (c,d) *S. aureus* biofilm on (a, c) pristine and (b, d) Silicone-g-AG4 films after pre-treatment with 1.0 mg/mL of FBG protein solution for 4 h. Scale bar is 10 μm.

FIG. S10 Effect of pristine silicone, Silicone-g-AG4, Silicone-g-AG-HEP1, and Silicone-g-HEP films on the viability of 3T3 fibroblasts. Viability is expressed as a percentage relative to the result obtained with the control (3T3 fibroblast cells incubated without any film present).

FIG. S11 A diagrammatical presentation of the advantageous effects achieved when a medical or veterinary device, typically but not exclusively, made of silicone is modified by coating same with an immobilized and cross-linked agarose coating, particularly, but not exclusively, a coating that is further modified by the addition of heparin.

Table 1 Surface composition as determined by XPS and water contact angle of the polymer-modified silicone films

DETAILED DESCRIPTION

2. Experimental Section
2.1 Materials

Medical grade silicone films were purchased from Bioplexus Inc. (Ventura, Calif., USA). All silicone Quinton™ peritoneal dialysis (PD) catheters were purchased from Tyco International Ltd. (Princeton, N.J., USA). Titanium (Ti) foils were purchased from Goodfellow Inc. (Huntingdon, UK). Polyurethane films were purchased from Central Polymer Engineering Supply (Singapore). All silicone Bardex® Foley urinary catheters were purchased from C. R. Bard Inc. (Murray Hill, N.J., USA). Agarose (AG) was purchased from Bio-Rad Laboratories (Hercules, Calif., USA). Sodium heparin (HEP) and 3-[4,5-dimethyl-thiazol-2-yl]-2,5-diphenyltetrazolium bromide (MTT) were purchased from Alfa Aesar Co. (Ward Hill, Mass., USA). Acryloyl chloride (97%), methacrylic anhydride (94%), bovine serum albumin (BSA), bovine plasma fibrinogen (FBG) and all solvents used (analytical grade) were purchased from Sigma-Aldrich (St. Louis, Mo., USA). *Escherichia coli* (*E. coli*, ATCC DH5a), *Staphylococcus aureus* (*S. aureus*, ATCC 25923), *Candida glabrata* (*C. glabrata*, ATCC CBS138) and 3T3 mouse fibroblast cells were purchased from American Type Culture Collection (Manassas, Va., USA). *Pseudomonas aeruginosa* (*P. aeruginosa*, PAO1) was purchased from National Collection of Industrial Food and Marine Bacteria (NCIMB, Buckshurn, Aberdeen, Scotland). The acrylated AG was prepared using similar procedures described in the literature.[13] Briefly, 1.0 g of AG was dissolved in 25 mL of N,N-dimethylacetamide (DMAC) at 100° C. After AG was dissolved completely, the solution was cooled to 0° C. in an ice-water bath. Then, 0.125 mL of acryloyl chloride in 2.5 mL DMAC was added dropwise into the AG solution with stirring. The reaction was allowed to proceed for 1 h at 0° C. and for another 4 h at 25° C. The acrylated AG product was precipitated in an excess volume of acetone and washed thoroughly with acetone followed by drying under reduced pressure. The methacrylated HEP was prepared using a procedure similar to that described in the literature.[14] Two hundred mg of HEP were dissolved in 10 mL of doubly distilled water. Then, 10 μL of methacrylic anhydride was added in the solution, and the pH of the solution was adjusted to 8.5 using 4 M NaOH solution. The solution was left to react overnight at 0° C. with stirring. The methacrylated HEP product was precipitated in an excess volume of cold ethanol followed by dialysis against water for 72 h using a dialysis tubing (molecular weight cut-off of 1000, Spectrum Laboratories Inc., Rancho Dominguez, Calif., USA). The methacrylated HEP solution was freeze-dried after dialysis.

2.2 Preparation of Agarose (AG), Heparin (HEP) and AG-HEP Grafted Films and Catheters For the preparation of cross-linked AG grafted silicone films (Silicone-g-AG), medical grade silicone film was cut into 2×2 $cm^2$ pieces and ultrasonically cleaned in isopropanol, ethanol and doubly distilled water for 10 minutes in each step. The clean silicone films were subjected to oxygen plasma for 5 min in an Anatech SP100 plasma system. The oxygen plasma treated films were then exposed to the atmosphere for another 10 minutes to promote the formation of peroxide groups on the plasma-treated surfaces. These peroxide groups served as active sites to initiate the subsequent UV-induced immobilization and cross-linking reaction for grafting acrylated AG onto the oxidized surfaces. Two hundred μL of acrylated AG aqueous solution (5 wt. %) were dropped onto the surface of the plasma-treated silicone film which was placed on a SCS P6206 spincoater. Spin-coating was carried out at a speed of 1000 rpm for 60 s. The procedure was then repeated for the other surface of the film. The silicone film with spin-coated acrylated AG was then placed in a Pyrex glass tube and degassed with argon for 30 min. The glass tube was sealed and irradiated with UV light in a Riko rotary photochemical reactor (Model RH400-10W) for 15, 30, 60 and 120 min to obtain the Silicone-g-AG1, Silicone-g-AG2, Silicone-g-AG3 and Silicone-g-AG4 films (Table 1), respectively. After irradiation, the Silicone-g-AG films were washed thoroughly with doubly distilled water at 60° C. for 24 h to remove the physically adsorbed acrylated AG. The HEP modified silicone films (Silicone-g-HEP) and AG-HEP modified silicone films (Silicone-g-

AG-HEP) were similarly prepared using the methacrylated HEP solution, and a mixture of acrylated AG and methacrylated HEP solutions with different ratios as indicated in Table 1, respectively. The uncross-linked AG coated silicone films (Silicone-c-AG) were similarly prepared using the unmodified AG solution. The concentration of acrylated AG, methacrylated HEP and unmodified AG in the solutions used was fixed at 5 wt. %.

The preparation procedures for the cross-linked AG grafted and AG-HEP grafted Ti foils and polyurethane films were similar to those for the AG grafted silicone films. Ti foil was cut into 1×1 cm$^2$ pieces and ultrasonically cleaned in Kroll's reagent (4.0% HF, 7.2% HNO$_3$, 88.8% water), dichloromethane, acetone and water in that order for 10 min in each step before grafting with AG or AG-HEP, while polyurethane film was cut into 2×2 cm$^2$ pieces and ultrasonically cleaned in ethanol and water for 10 min in each step. Thereafter, spin-coating and UV irradiation were employed as described above.

For the preparation of AG and AG-HEP grafted silicone catheter, the PD catheter was cut into 6 cm segments and washed with isopropanol, ethanol and water as described above. In order to activate both the extra-luminal and intra-luminal surfaces of the catheter segments, ozone was used instead of oxygen plasma. After pretreatment with an oxygen-ozone gas mixture (generated from an Azcozon ozone generator (Model VMUS-4PSE) at an oxygen inlet flow rate of 60 L/h, and ozone production rate of about 3.6 g/h.) for 20 min, the ozone-treated catheter segment was introduced into a Pyrex glass tube containing the respective reagent (AG or AG-HEP at 5 wt. %) as described above and degassed with argon for 30 min. The glass tube was sealed and heated to and then maintained at 70° C. in an oil bath for 8 h. After the reaction, the AG or AG-HEP modified catheter segment was washed with doubly distilled water at 60° C. for 24 h. Urinary catheter segments (1 cm long) were similarly grafted with AG and AG-HEP via ozone pretreatment, exposure to the respective reagent and UV irradiation.

Cross-linked AG hydrogel (without silicone film) was prepared by adding 5 mg of 4,4'-azobis(4-cyanovaleric acid) to a Pyrex tube containing 10 mL of acrylated AG aqueous solution (5 wt. %). After purging with argon for 30 min, the flask was sealed and irradiated with UV light in a Riko rotary photochemical reactor for 120 min. After irradiation, the cross-linked AG hydrogel was washed with ethanol and doubly distilled water at 60° C. for 24 h followed by freeze-drying. Cross-linked AG-HEP hydrogel was similarly prepared using a mixture of acrylated AG and methacrylated HEP solution (acrylated AG:methacrylated HEP=9:1 (w/w)). Uncross-linked AG gel was prepared by heating the unmodified AG solution to 120° C. and cooled to 25° C. followed by freeze-drying.

2.3 Microbial Adhesion and Biofilm Formation Assay

Bacteria were cultured overnight in growth medium (tryptic soy broth for *S. aureus*, nutrient broth for *E. coli* and lysogeny broth for *P. aeruginosa*). The bacteria-containing growth broth was then centrifuged at 2,700 rpm for 10 min to remove the supernatant. The bacterial cells were washed with PBS (pH 7.4) and resuspended in PBS at a concentration of 10$^8$ cells/mL, as estimated from optical density (OD) at 540 nm (OD of 0.1 at 540 nm is equivalent to ~10$^8$ cells/mL based on spread plate counting). The pristine and modified silicone films of size 1×1 cm$^2$ were placed in a 24-well plate and covered with 1 mL bacterial suspension at 37° C. for 4 h. After the bacterial adhesion process, the films were washed thrice with PBS to remove the non-adherent bacteria. For the quantification of adherent bacteria, the spread plate method was carried out as described in the literature.[15] Briefly, the films with adherent bacteria were put into 2 mL of PBS and ultrasonicated for 7 min followed by vortexing for 30 s to release the bacterial cells into the PBS. The bacterial suspension was serially diluted and spread on an agar plate. After culturing overnight, the number of viable bacterial cells was quantified by counting the number of colonies on the agar plate. For scanning electron microscopy (SEM) observation, the adherent bacteria on the films were fixed with 3 vol. % glutaraldehyde in PBS overnight at 4° C. After serial dehydration with 25%, 50%, 75% and 100% ethanol for 10 min each, the films were dried under reduced pressure, coated with platinum, and observed under SEM. For the assessment of the viability of adherent bacteria on pristine and modified silicone, the films were stained by a combination dye (LIVE/DEAD BacLight Bacterial Viability Kit) and observed under a Leica DMLM microscope equipped with a 100 W Hg lamp.

For the assessment of biofilm formation by *S. aureus*, *E. coli* and *P. aeruginosa*, overnight bacterial culture broth was diluted to a concentration of 10$^7$ cells/mL with their respective growth medium. The pristine and modified substrates (1×1 cm$^2$ films or 1 cm catheter segments) were placed in a 24-well plate and covered by 1 mL of bacterial suspension at 37° C. for 48 h to allow biofilm growth. After the biofilm growth period, the substrates were washed thrice with PBS. The films were observed under SEM, and the number of biofilm bacterial cells on the films and catheter segments (both intraluminal and extraluminal surfaces) was quantified using the spread plate method as described above.

For the assessment of biofilm formation by *C. glabrata*, overnight fungal culture broth was diluted to a concentration of 10$^7$ cells/mL. The pristine and modified substrates (1×1 cm$^2$ films) were placed in a 24-well plate and covered by 1 mL of fungal suspension at 37° C. After 1.5 h, the fungal suspension was removed and the substrates were washed twice with PBS. One mL of fresh culture medium was then placed over the substrates at 37° C. for 24 h to allow fungal biofilm growth. After the biofilm growth period, the substrates were fixed with 3 vol. % glutaraldehyde in PBS and subjected to serial dehydration with 25%, 50%, 75% and 100% ethanol and observed under SEM.

2.4 Stability Tests

The stability of the AG and AG-HEP graft layer on the silicone films was assessed by aging the films in lysozyme aqueous solution (10 µg/mL) for 30 days at 37° C. The lysozyme concentration was selected to simulate its concentration in human serum. After the aging period, assessment of bacterial biofilm formation on the films was carried out as described above to test the stability of the coating. For comparison purposes, the degradation of as-prepared AG and AG-HEP hydrogel (without silicone film) in lysozyme solution was also carried out. One hundred mg of the dry AG and AG-HEP hydrogel were aged in 10 mL of lysozyme solution (10 µg/mL) for 30 days at 37° C. After the aging period, the hydrogel was dialyzed against water for 72 h using a dialysis tubing (molecular weight cut-off of 3500, Spectrum Laboratories Inc., Rancho Dominguez, Calif., USA) followed by freeze-drying. The degree of weight loss (WL) was calculated as follows:

$$WL=(WB-WA)/WB\times100\% \quad (1)$$

where WB and WA are the weight of hydrogel before and after aging, respectively.

The stability of the modified PD catheter under frictional forces was carried out by pulling the catheter segments between two pieces of raw meat (pork). The meat was fixed between two PMMA plates of length of 5 cm. A modified catheter segment of 6 cm length was inserted between the two pieces of meat from one side and pulled out from the other side. This procedure was repeated 5 times. After the friction test, the catheter segment was cut into 1 cm length and assay of bacterial biofilm formation on the catheter segment was carried out as described above to test the stability of the grafted layer. The 6 cm modified catheter segments were also subjected to bending tests whereby the segment was bent into a circle upwards and downwards 15 times. After the bending test, the middle 3 cm of the catheter, which was subjected to the highest bending stress, was cut into three segments of 1 cm length, and assay of bacterial biofilm formation on the these segments was then carried out.

2.5 Protein Adsorption

Pristine and modified silicone films of size 2×2 cm$^2$ were first equilibrated for 1 h in CPBS (citrate-phosphate buffer saline, PBS and 0.01 M sodium citrate, pH 7.4), and then immersed in pure BSA or FBG protein solution (1.0 mg/mL in CPBS) for 4 h at 37° C. After this protein adsorption period, the films were washed with CPBS and doubly distilled water twice, respectively. The modified dye-interaction method was employed to determine the amount of adsorbed protein on the films with Bio-Rad protein dye reagent (Catalog No. 500-0006) using a similar procedure as that described in the literature.[16] Briefly, protein solutions (0.4 mL) of different known concentrations were added to 10 mL of the 5-time diluted stock dye solution. After 10 min, centrifugation was carried out at 5000 rpm for 15 min, and the absorbance of the supernatant of the protein-dye solutions at 465 nm was used to obtain a standard calibration curve. For the quantification of adsorbed protein on the film, the film was put in 10 mL of the dye solution. After 3 h of immersion, the film was removed. The remaining solution was centrifuged and the absorbance of the supernatant was measured at 465 nm. The amount of adsorbed protein on the films was calculated from the standard calibration curve.

2.6 Cytotoxicity Assay

The cytotoxicity of the modified silicone films was investigated using the standard MTT assay. DMEM supplemented with 10% fetal bovine serum, 1 mM L-glutamine, 100 IU/mL penicillin was used to culture 3T3 fibroblast cells. One mL medium containing the DMEM 3T3 fibroblasts at a density of 10$^4$ cells/mL were placed in each well of a 24-well plate. The plate was then incubated in a humidified atmosphere of 95% air and 5% CO$_2$ at 37° C. for 24 h. After replacing the medium with a fresh one, the films of size 1×1 cm$^2$ were gently placed on top of the cell layer in the well. The control experiment was carried out using the complete growth culture medium without the film (nontoxic control). After incubation for another 24 h at 37° C., the culture medium and film in each well was removed. Nine hundred μL of medium and 100 μL of MTT solution (5 mg/mL in PBS) were then added to each well. After 4 h of incubation, the MTT solution and medium was removed and 1 mL of dimethyl sulfoxide (DMSO) was added to dissolve the formazan crystals. The optical absorbance at 570 nm was then measured on a BIO-TEK microplate reader (Model Powerwave XS). The results were expressed as percentages relative to the optical absorbance obtained in the control experiment.

2.7 Cell Adhesion

Pristine and modified silicone films of size 1×1 cm$^2$ were placed in a 24-well plate. One mL of culture medium containing 3T3 fibroblasts at a density of 2×10$^5$ cells/mL was added and incubated for 24 h. After the incubation period, the films were rinsed thrice with medium to remove non-adherent cells. The film surfaces with adherent cells were viewed using a Leica DMLM microscope. For quantification of adherent 3T3 fibroblast cells, the films with adherent cells were placed in a 24-well plate and MIT assay was carried out. A standard calibration curve was generated by seeding a known number of 3T3 fibroblast cells in a 24-well plate and incubating for 4 h at 37° C. followed by MTT assay. The number of 3T3 fibroblasts adhered on the films was calculated from the standard calibration curve.

2.8 Platelet Adhesion

Fresh blood collected from a healthy rabbit was immediately mixed with 3.8 wt % sodium citrate solution in a ratio of 9:1 (v/v). Platelet-rich plasma (PRP) was obtained by centrifuging the blood at 700 rpm and 8° C. for 10 min. The PRP was diluted with PBS in a ratio of 1:1 (v/v), and 0.1 mL of the diluted PRP was introduced on the surface of a 1×1 cm$^2$ silicone film. After incubation at 37° C. for 1 h, the film was washed thrice with PBS. The adherent platelets were then fixed with 3 vol % glutaraldehyde in PBS solution overnight at 4° C. After serial dehydration with 10%, 25%, 50%, 75%, 90% and 100% ethanol for 10 min each, the films were dried under reduced pressure, coated with platinum, and observed under SEM. The number of platelets on the films was quantified by counting the total number of adherent platelets from representative SEM images at the same magnification (×2,000).[17] The results obtained from the modified films were normalized by that from pristine silicone.

2.9 Plasma Recalcification Time (PRT)

Fresh blood from a healthy rabbit mixed with 3.8 wt % sodium citrate solution was prepared as described above. The platelet poor plasma (PPP) was obtained by centrifuging the blood at 3,000 rpm and 8° C. for 20 min, and 0.1 mL of the PPP was introduced on the surface of a 2×2 cm$^2$ silicone film. After the film was incubated at 37° C. for 10 min, 0.1 mL of 0.025 M CaCl$_2$ aqueous solution at 37° C. was then added to the PPP on the silicone film. The PPP solution was monitored for clotting by manually dipping a stainless-steel wire hook coated with silicone into the solution to detect fibrin threads. The PRT was recorded at the first appearance of silky fibrin.

2.10 Hemolysis Test

Silicone film of size 1×1 cm$^2$ and 10 mL of PBS was introduced into a BIOLOGIX® centrifuge tube. After the tube was incubated at 37° C. for 1 h, 0.2 mL of diluted rabbit blood (8 mL of blood mixed with 10 mL of PBS) was added and the tube was incubated at 37° C. for another 1 h. PBS and doubly distilled water were used for negative and positive controls, respectively. The tube was then centrifuged at 1,500 rpm for 10 min and the optical absorbance of the supernatant was measured at 545 nm on a HITACHI spectrophotometer (Model U-2800). The hemolysis rate (HR) was calculated as follows:

$$HR=(AS-AN)/(AP-AN) \qquad (2)$$

where AS, AN and AP are the optical absorbance of the supernatant of the solution containing film, the negative control and the positive control, respectively.

2.11 Characterization

Due to the curved surface of the catheter, characterization methods such as X-ray photoelectron spectroscopy (XPS) and contact angle measurement as well as SEM observation of adherent bacterial cells could not be easily carried out on its surface. Thus, flat medical grade silicone sheet was selected as a model surface, and after modification, investigation of the coating characteristics was carried out. The surface chemical composition of the silicone films was analyzed by XPS on an AXIS Ultra$^{DLD}$ spectrometer (Kratos Analytical Ltd., UK) with a monochromatic Al Kα X-ray source (1486.71 eV photons). The silicone film surfaces were observed by SEM (JEOL, Model 5600 LV), and the cross-sections of films and catheters were observed by field emission scanning electron microscopy (FESEM, JEOL, Model JSM-6700) and SEM, respectively. The samples were fixed on the SEM metal stubs using double-sided carbon tapes and sputter-coated with a thin platinum layer to enhance the contrast and quality of the images prior to SEM and FESEM observation. The concentration of the immobilized heparin on the modified films was quantified using the toluidine blue method as described previously.[18] Static contact angles of the different surfaces were measured at room temperature by the sessile drop method using a 3 μL water droplet in a Rame-Hart telescopic goniometer (Model 100-00-(230)). For each sample, three measurements from different regions of a surface were taken, and at least three independent tests were carried out with triplicate samples each time.

2.12 Statistical Analysis

The results were reported as mean±standard deviation (SD) and were assessed statistically using one-way analysis of variance (ANOVA) with Tukey post hoc test. Statistical significance was accepted at P<0.05.

3. RESULTS AND DISCUSSION 3.1 Surface Characterization

Figure 2:
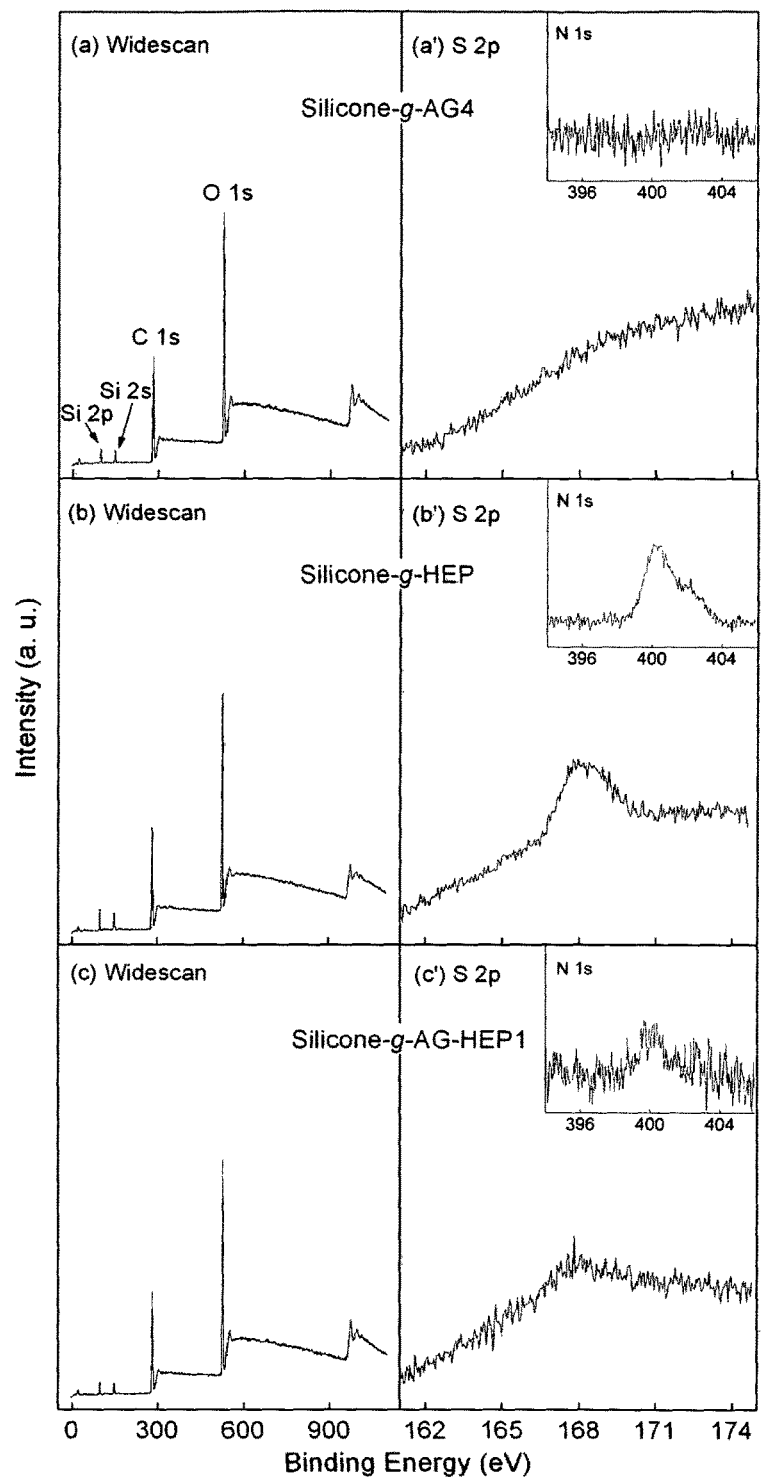
FIG. 2 XPS widescan and S 2p core-level spectra of the (a, a') Silicone-g-AG4, (b, b') Silicone-g-HEP and (c, c') Silicone-g-AG-HEP1 films. The insets show the N 1s core-level spectrum of respective film. The intensity of the Si 2p and Si 2s signals in the widescan spectrum of the crosslinked AG grafted silicone film, Silicone-g-AG4, (FIG. 2($a$)) is significantly decreased as compared to that of the pristine silicone film (FIG. S1($a$)), indicating the successful grafting of AG on the silicone film.

The procedures for the covalent grafting and crosslinking of AG and AG-HEP polymers on the silicone surfaces are illustrated schematically in FIG. 1. The peroxides and hydroxyl peroxides on the silicone surface generated by oxygen plasma or ozone treatment served as anchor sites for the subsequent immobilization of the polymer chains.[19] The XPS widescan, S 2p core-level and N 1s core-level spectra of the AG, HEP and AG-HEP grafted silicone films are shown in FIG. 2. The intensity of the Si 2p and Si 2s signals in the widescan spectrum of the Silicone-g-AG4 film (FIG. 2(a)) is significantly decreased as compared to that of the pristine silicone film (FIG. S1(a)), indicating the successful grafting of AG on the silicone film. As expected, no sulfur and nitrogen signals are discernible in the S 2p core-level and N 1s core-level spectra of the Silicone-g-AG4 film (FIG. 2(a') and its inset, respectively) since these elements are not present in silicone or acrylated AG polymer. The surface elemental compositions of the pristine and polymer-modified silicone as determined by XPS are shown in Table 1. The [Si]/[C] ratio of the Silicone-g-AG4 film is about 0.08:1 and is much lower than that of the pristine silicone (0.52:1). The extent of AG grafting can be qualitatively estimated from the [Si]/[C] ratio since Si is present only in silicone and not in the acrylated AG. As shown in Table 1, the [Si]/[C] ratios of Silicone-g-AG1, Silicone-g-AG2, Silicone-g-AG3 and Silicone-g-AG4 films decrease with increasing UV irradiation time from 15 min to 120 min, indicating an increase in the grafting density of the immobilized AG.

For the Silicone-g-HEP film, sulfur and nitrogen signals are present in the S 2p core-level and N 1s core-level spectra (FIG. 2(b') and its inset, respectively) after 120 min of UV-induced grafting of methacrylated HEP. In addition, the [Si]/[C] ratio of the Silicone-g-HEP film decreased to 0.14:1, which also confirms the successful grafting of HEP on the silicone film. The surface concentration of immobilized HEP, as determined by the toluidine blue method, was 12.1 μg/cm$^2$ of the Silicone-g-HEP film.

Figure 3:
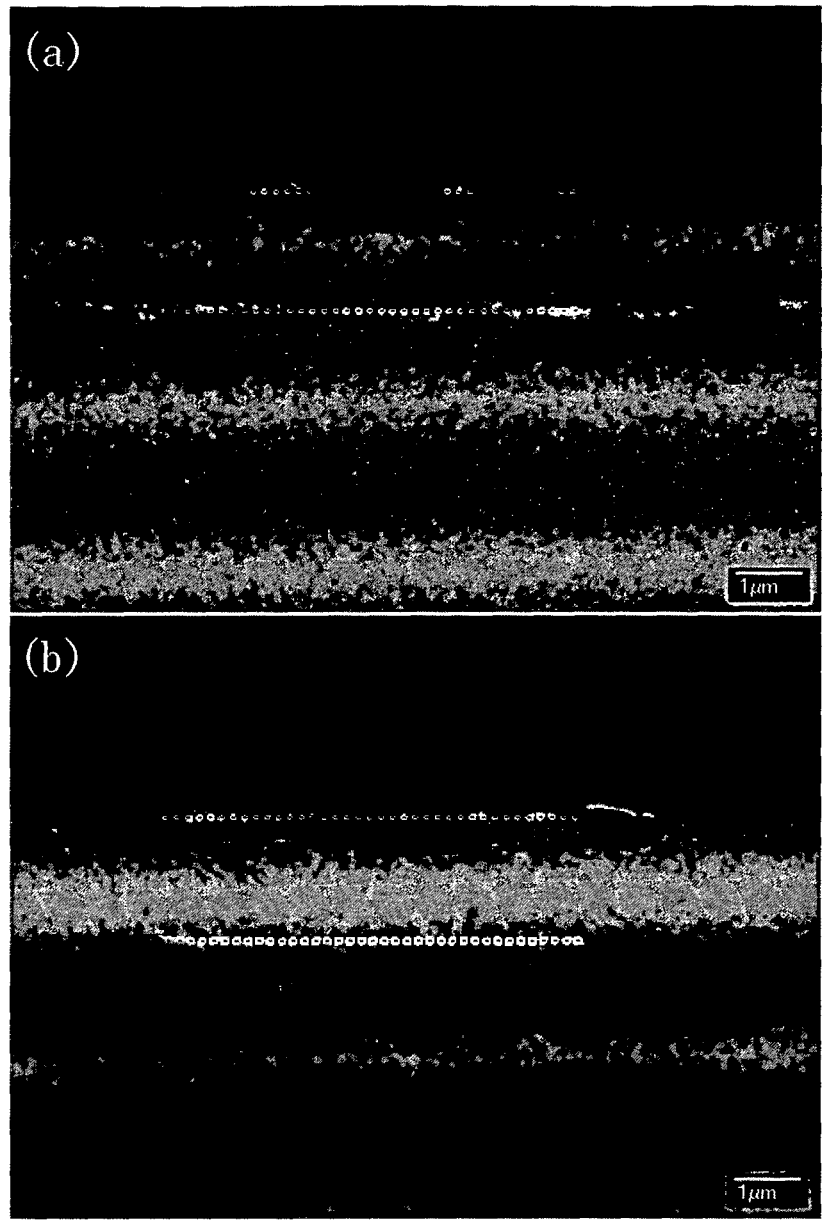
FIG. 3 FESEM images of the cross-section of (a) Silicone-g-AG4 and (b) Silicone-g-AG-HEP1 films. Scale bar is 1 μm.

For the Silicone-g-AG-HEP1 film, the sulfur and nitrogen signals are discernible in the S 2p core-level and N 1s core-level spectra (FIG. 2(c') and its inset, respectively). The [Si]/[C] ratio of the Silicone-g-AG-HEP1 film decreased to 0.10:1. FIG. 3 shows the FESEM images of the cross-section of the AG and AG-HEP modified films. It can be clearly observed that the thickness of the grafted AG layer (upper layer in FIG. 3(a)) on Silicone-g-AG4, and the AG-HEP layer (upper layer in FIG. 3(b)) on Silicone-g-AG-HEP1 is ~2 μm, confirming the successful grafting of AG and AG-HEP on the silicone surface. The thickness of the grafted AG layer can be varied by changing the UV irradiation time. When the UV irradiation time was decreased to 60 min and 15 min, the thickness of the grafted AG layer decreased to 0.8 μm and 0.3 μm, respectively. The surface concentration of the immobilized HEP increases with increasing feed ratio of methacrylated HEP in the reaction solution (compare the immobilized HEP concentration of Silicone-g-AG-HEP1 and Silicone-g-AG-HEP2 in Table 1), which is also confirmed by the increase in [S]/[C] and [N]/[C] ratios of these films in Table 1.

The change in water contact angle of the pristine and polymer-modified silicone also provides supporting evidence that the silicone film surface has been successfully modified. As shown in Table 1, the pristine silicone film is hydrophobic with a water contact angle of 107°. The modified silicone films after grafting with AG, HEP and AG-HEP become hydrophilic with a much lower water contact angle. In addition, it can be observed that the contact angle of the AG-modified silicone films decreases with the increasing of UV reaction time, indicating an increase in the grafting density of the immobilized AG, which is consistent with the results revealed by the surface [Si]/[C] ratios of these films (Table 1).

3.2 Microbial Adhesion and Biofilm Formation Assay

Figure 4:
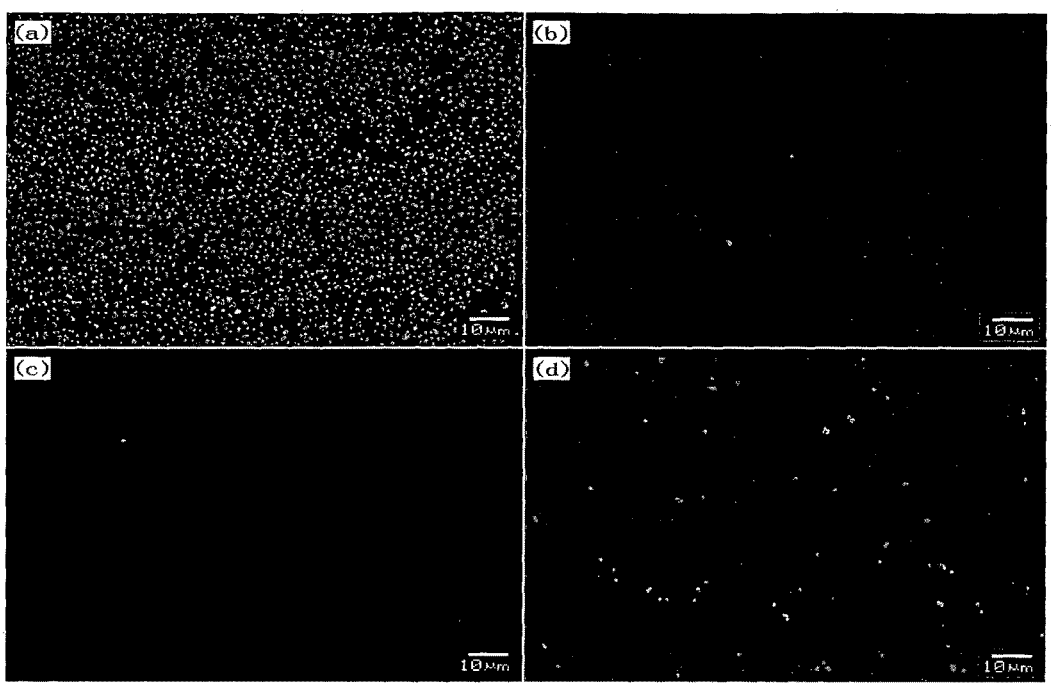
FIG. 4 SEM images of (a) pristine silicone, (b) Silicone-g-AG4, (c) Silicone-g-AG-HEP1 and (d) Silicone-g-HEP film surfaces after exposure to a PBS suspension of $S.$ $aureus$ ($10^8$ cells/mL) for 4 h. Scale bar is 10 μm.

Development of surface resistance to bacterial adhesion is a crucial step to prevent bacterial infection. After adhesion on a surface, bacteria will multiply and form biofilm in the presence of a growth medium. The biofilm in turn protects the bacterial cells from the host's natural defense systems as well as antibiotics. For an implanted device, such as a PD catheter, the first few hours after insertion is considered an important period where the introduced pathogen is still in the quiescent stage and the host immune system can actively neutralize the invading pathogen. The efficacy of the polymer-modified silicone film in reducing bacterial adhesion was evaluated using the model bacteria, Gram-positive *S. aureus* and Gram-negative *E. coli*, because they are among the most common species responsible for PD-related infections. FIG. 4 shows the SEM images of adherent *S. aureus* cells on pristine and modified silicone films. A large number of *S. aureus* was observed on pristine silicone after 4 h of incubation in PBS (FIG. 4(a)). The number of adherent *S. aureus* was significant reduced after the surface modification of silicone film with AG, AG-HEP and HEP (FIG. 4(b-d)). It is well-known that microbes prefer to attach to hydrophobic surfaces due to hydrophobic interactions.[20] Thus, the ability of the AG, AG-HEP and HEP modified silicone to inhibit *S. aureus* adherence can be attributed to the improved surface hydrophilicity which results from the grafting of the hydrophilic polymers. Thus, the AG and HEP polymers are anti-adhesive, but not bactericidal. The anti-adhesive property of the AG-modified silicone strongly depends on the grafting density of the immobilized AG layer, which is associated with the UV-induced grafting time (FIG. S2). The efficacy in inhibiting *S. aureus* and *E. coli* adhesion increases with the increasing UV irradiation time. After 120 min of UV induced grafting, the resulting Silicone-g-AG4 reduced *S. aureus* and *E. coli* adhesion by ~98% and ~99%, respectively.

HEP is less effective in reducing *S. aureus* adhesion than AG (comparing FIG. 4(d) with 4(b)). Thus, the grafting of a large amount of HEP on AG-HEP-modified silicone will result in an increase in the number of adherent bacteria. If the surface concentration of immobilized HEP is restricted to 2.6 µg/cm$^2$ or less, the antibacterial efficacy of Silicone-g-AG-HEP will not be significantly different from that of Silicone-g-AG4 (comparing the number of adherent bacteria on the Silicone-g-AG-HEP films with different surface concentrations of HEP in FIG. S3).

Figure 5:
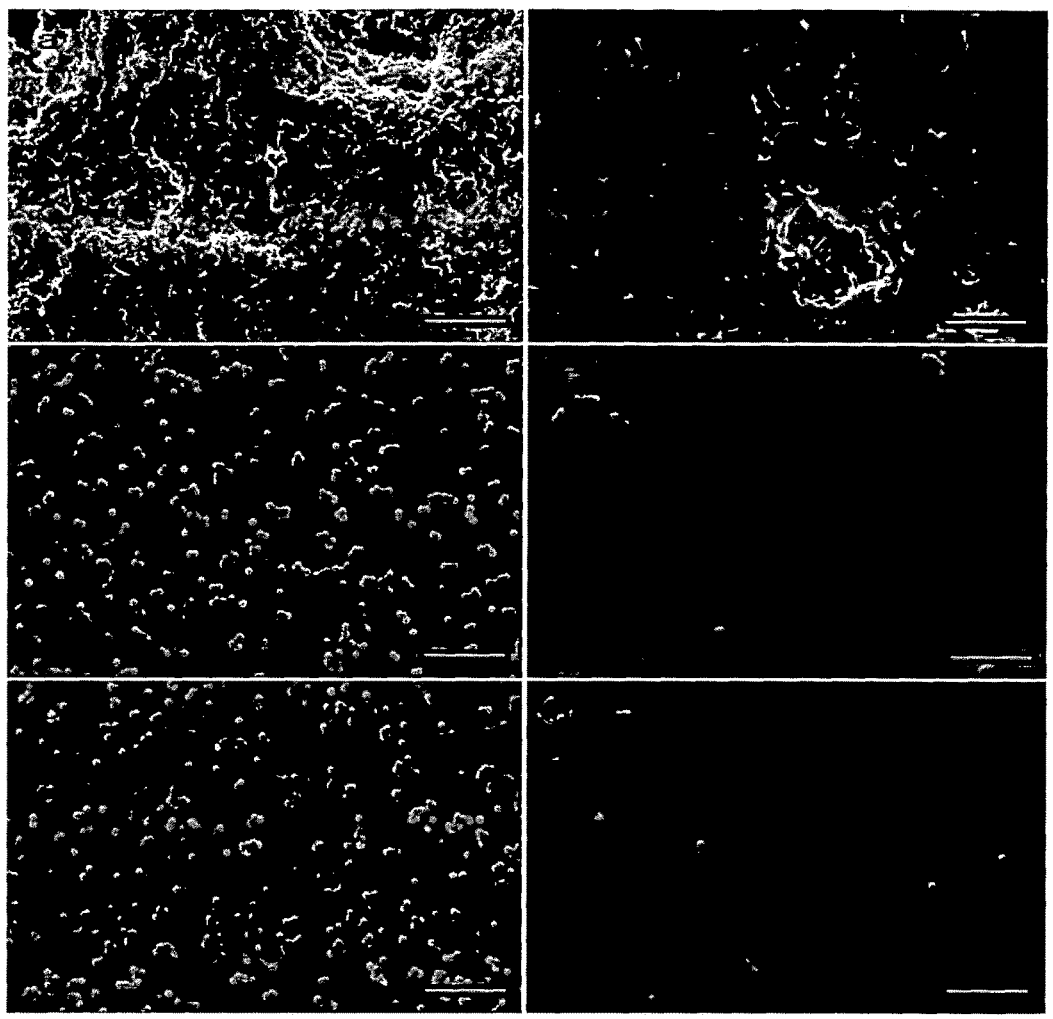
FIG. 5 SEM images of (a-c) $S.$ $aureus$ and (d-f) $E.$ $coli$ biofilm on (a, d) pristine, (b, e) Silicone-g-AG4 and (c, f) Silicone-g-AG-HEP1 films after incubation in growth medium containing $10^7$ bacterial cells/mL for 48 h. Scale bar is 10 μm.
Figure 6:
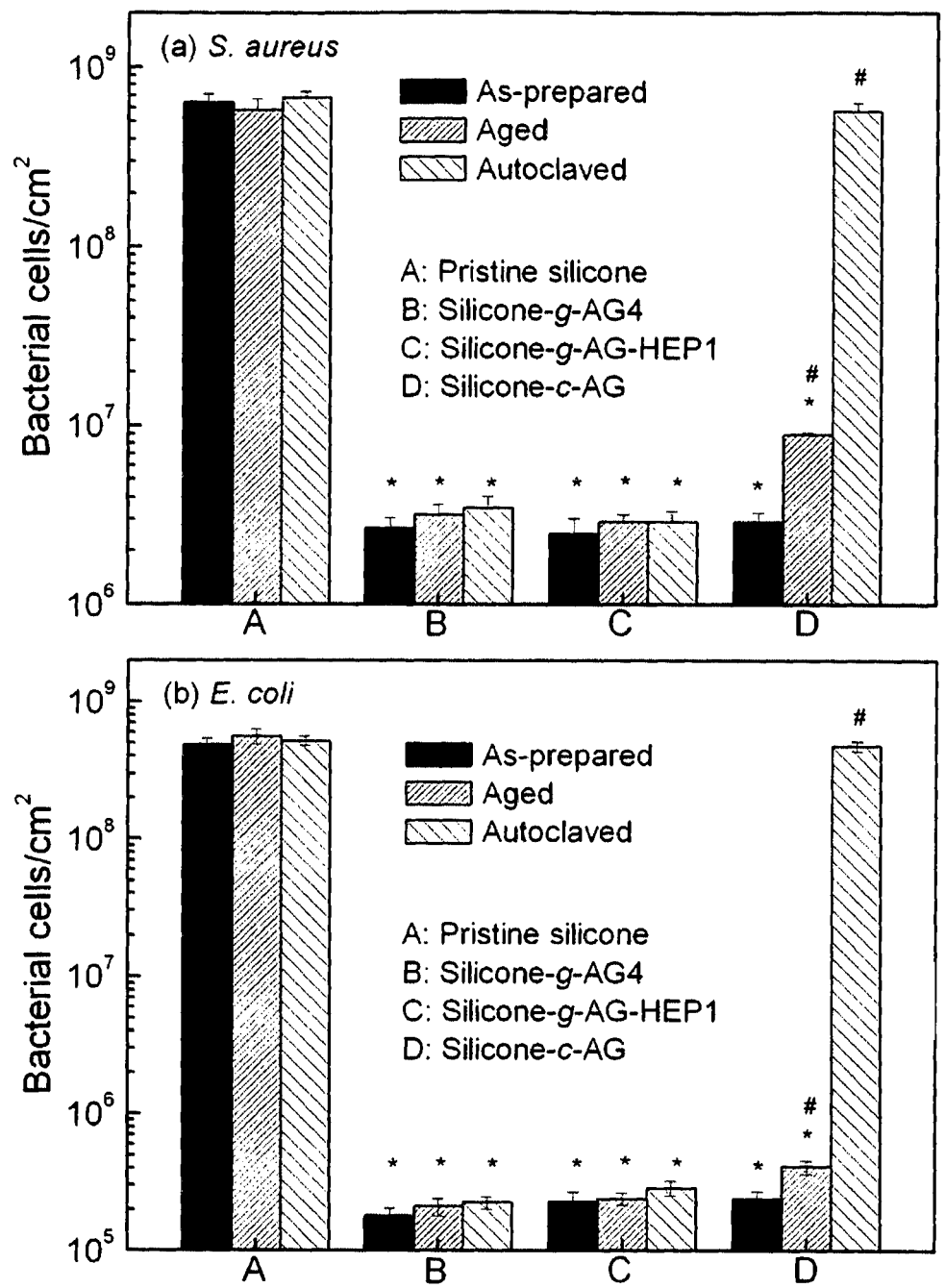
FIG. 6 Quantitative count of adherent (a) $S.$ $aureus$ and (b) $E.$ $coli$ cells per $cm^2$ on the pristine and modified film surfaces after incubation in growth medium containing $10^7$ bacterial cells/mL for 48 h as determined by the spread plate method. * Significant differences (P<0.05) compared with pristine silicone.# Significant differences (P<0.05) compared with respective as-prepared film.

Bacterial and fungal biofilms are the major cause of peritonitis and other PD catheter-related infections in PD dialysis. Similarly, biofilm formation on central venous catheters and urinary catheters increases the risk of CABSIs and CAUTIs, respectively. In this work, the efficacy of the polymer-modified silicone films in inhibiting bacterial biofilm formation was assessed after incubation in growth medium containing 10$^7$ bacterial cells/mL for 48 h. FIG. 5 shows the SEM images of bacterial biofilm on pristine and modified silicone surfaces. It can be seen from FIGS. 5(a) and 5(d) that both *S. aureus* and *E. coli* readily form a thick biofilm on the pristine silicone film. After surface grafting of AG on the silicone surface, significant reduction in bacterial biofilm was observed. There is no obvious *S. aureus* biofilm but some bacterial clusters are present on the Silicone-g-AG4 and Silicone-g-AG-HEP1 films (FIGS. 5(b) and 5(c), respectively). The Silicone-g-AG4 and Silicone-g-AG-HEP1 films are even more effective in preventing *E. coli* biofilm formation, and only a few individual bacterial cells can be observed (FIGS. 5(e) and 5(f), respectively). These results suggest that *S. aureus* biofilm formation on silicone surface is more difficult to prevent than *E. coli* biofilm, which is consistent with a previous report.[21] Nevertheless, quantification of the number of adherent bacteria on pristine and modified silicone films showed that the modified silicone (Silicone-g-AG4 and Silicone-g-AG-HEP1) reduced the number of adherent *S. aureus* and *E. coli* by ~2.4 and ~3.3 orders of magnitude, respectively (FIGS. 6(a) and 6(b)), compared to the pristine film. In addition to *E. coli* and *S. aureus*, Gram-negative *P. aeruginosa* biofilm formation on the AG and AG-HEP modified silicone films was also assessed since *P. aeruginosa* is another major cause of infection in PD dialysis. The number of adherent *P. aeruginosa* cells on the AG and AG-HEP modified films was reduced by more than 2 orders of magnitude compared to pristine silicone (FIG. S4). Thus, the bacterial adhesion and biofilm formation assays indicate that the AG and AG-HEP graft layers are effective against both Gram-positive and Gram-negative bacterial species.

Fungal infection is a more severe PD-related infection than bacterial infection in terms of mortality and morbidity, with up to 44% death rate in infected PD patients.[22] The efficacy of the AG-modified silicone films in inhibiting fungal biofilm formation was assessed and the SEM image results are shown in FIG. S5. As shown in FIG. S5(a), *C. glabrata* readily adhered and formed a number of clusters on the pristine silicone film. After surface grafting of AG on the silicone surface, a significant reduction in the number of fungal cells and clusters was observed (FIG. S5(b)), indicating that the AG coating is effective in the inhibition of fungal biofilm formation.

Figure 7:
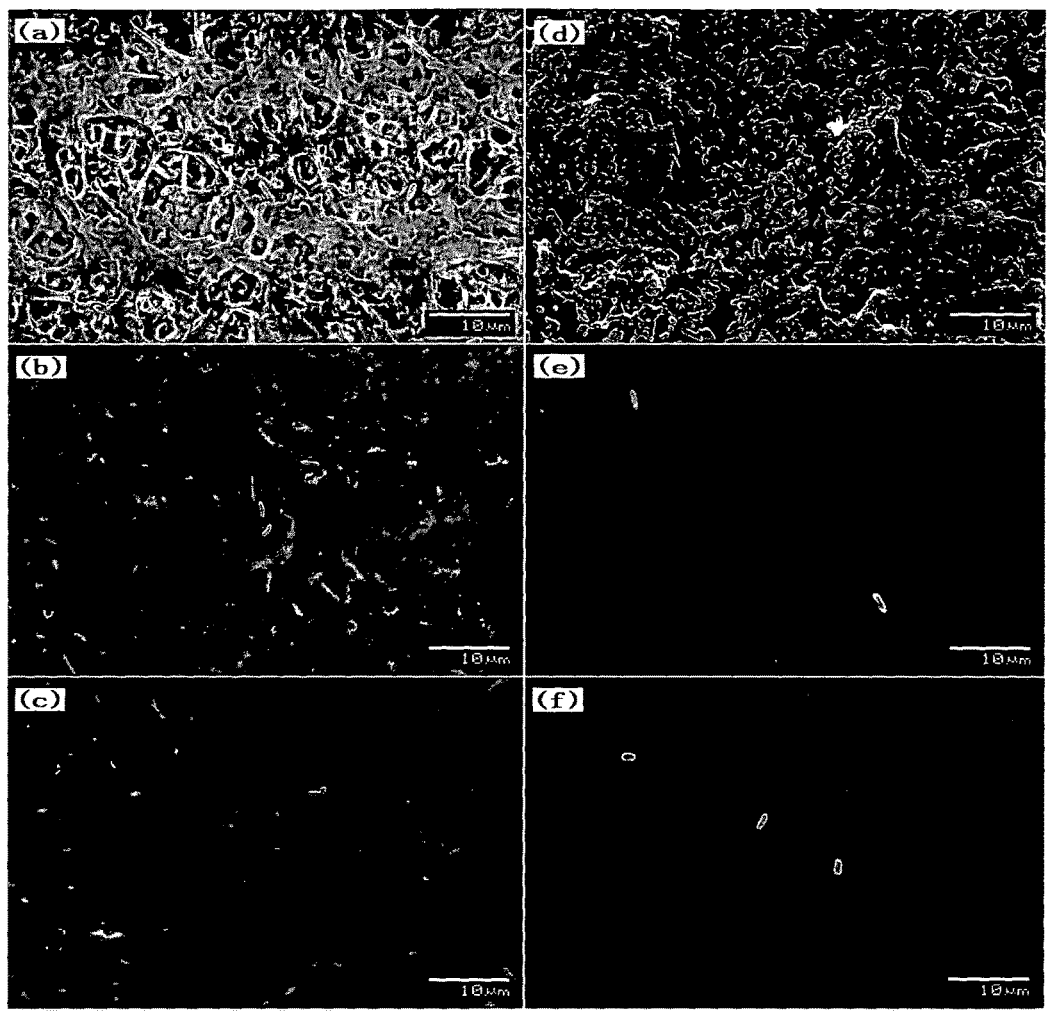
FIG. 7 SEM images of $E.$ $coli$ biofilm on (a) pristine titanium foil, (b) AG modified titanium foil, (c) AG-HEP modified titanium foil, (d) pristine polyurethane film, (e) AG modified polyurethane film and (f) AG-HEP modified polyurethane film after incubation in growth medium containing $10^7$ bacterial cells/mL for 48 h. Scale bar is 10 μm.

The corresponding results obtained with the AG and AG-HEP modified Ti foils and polyurethane films exposed to *E. coli* in growth medium are shown in FIG. 7.

Comparing the results in this FIG. with FIGS. 5(d) to 5(f), it can be concluded that the AG and AG-HEP graft layers are equally effective in inhibiting biofilm formation on Ti and polyurethane as on silicone.

In addition to the flat silicone film surface, the AG and AG-HEP polymer were grafted onto tubular PD catheter surface via ozone treatment followed by heat-induced immobilization and crosslinking of the polymer layer. By changing the heating period, the thickness of the AG graft layer can be varied. This is illustrated in FIGS. S6(a) and S6(b), which show the cross-section of AG-modified PD catheter prepared using a heating period of 8 h and 18 h, respectively. These heating periods resulted in AG graft layer of ~2 and ~5 µm thickness, respectively. FIG. S6(c) shows the number of adherent *E. coli* cells on the pristine and modified catheter surfaces after 48 h of incubation in culture medium. The AG and AG-HEP modified PD catheters reduced the number of adherent bacterial cells by more than 3 orders of magnitude, similar to the results obtained with the Silicone-g-AG4 film. In addition, no significant difference in the number of adherent bacterial cells was found on the modified catheters with 2 µm and 5 µm of polymer graft layer, indicating that there is no substantial improvement in the antibacterial efficacy of the AG and AG-HEP coatings beyond 2 µm thickness. Grafting of AG and AG-HEP polymer onto tubular urinary catheter surface via ozone treatment followed by UV-induced immobilization was also tested. FIG. S7 shows that the modified urinary catheter segments also reduced bacterial colonization very significantly.

3.3 Stability

If coatings are applied on catheters, their stability is a crucial requirement since catheters may be placed in the body for a long time. The stability of the AG and AG-HEP modified silicone films were assessed by conducting the bacterial biofilm assay on the films after they were aged in lysozyme solution at 37° C. for 30 days. As shown in FIG. 6(a), the number of adherent *S. aureus* after the biofilm assay increased slightly but not significantly ($P>0.05$) on the aged AG and AG-HEP modified films. Similar results were also obtained for *E. coli* (FIG. 6(b)). In addition, the biofilm formation assay also shows that the Silicone-g-AG4 and Silicone-g-AG-HEP1 films maintain their antibacterial property after autoclaving at 121° C. for 20 min (FIGS. 6(a) and 6(b)). These results suggest that the cross-linked AG and AG-HEP layers on silicone are stable. The stability of the graft layer after aging for 30 days also indicates that the cross-linked AG and AG-HEP layers are able to prevent the hydrophobic recovery of silicone and retain their antibacterial efficacy.

A similar aging experiment in lysozyme solution for 30 days was carried out with cross-linked AG and AG-HEP hydrogels and uncross-linked AG hydrogel. For the cross-linked AG and AG-HEP hydrogels, a weight loss of 13.5% and 11.8%, respectively, was observed. The uncross-linked AG hydrogel showed a higher weight loss of 22.7%. Biofilm assay carried out with aged Silicone-c-AG film (uncross-linked AG coated silicone film) (FIG. 6) also confirmed that the uncross-linked AG coating is not as stable as the cross-linked one. In addition, the Silicone-c-AG film after autoclaving at 121° C. for 20 min does not possess antibacterial property since the uncross-linked AG layer was only physically adsorbed on the film and it melted away during autoclaving.

When a catheter is inserted into the body, it will encounter frictional and bending forces. The stability of the cross-linked AG and AG-HEP layer on the PD catheter after being subjected to such forces was evaluated using the bacterial biofilm formation assay and the results are shown in FIG. S8. The AG and AG-HEP modified catheters showed good stability since there is no significant change in the number of adherent bacteria on the modified catheter after the friction and bending tests.

3.4 Protein Adsorption and Cell Adhesion

Figure 8:
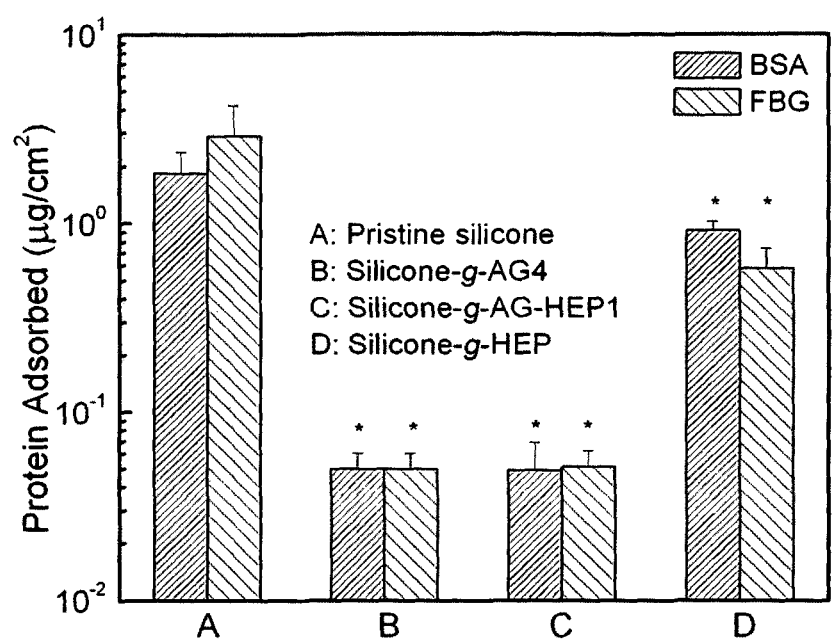
FIGS. 8 BSA and FBG adsorption on pristine silicone, Silicone-g-AG4, Silicone-g-AG-HEP1 and Silicone-g-HEP films after the films were treated with 1.0 mg/mL of pure protein solutions for 4 h. * Significant differences (P<0.05) compared with pristine silicone.

Omental wrapping is the leading cause of PD outflow failure in PD treatment. The omentum is the primary peritoneal defense organ, and in response to inflammation or foreign matter, it will adhere to and wall off the affected area. Protein adsorption on the surface of PD catheter is a crucial factor for omental wrapping since the mechanism for omental adhesion is believed to involve the formation of fibrin exudates at the site of assault, which attracts active migration of fibroblasts and leukocytes and finally leads to encapsulation of the affected area. In this work, the adsorption of two kinds of proteins, FBG and BSA, on the modified silicone films was investigated. As shown in FIG. 8, the amount of adsorbed FBG and BSA on pristine silicone film is ~2.9 and ~1.9 µg/cm², respectively. After grafting with AG, the protein adsorption was very significantly reduced. The Silicone-g-AG4 film reduced BSA and FBG adsorption by ~98%, and the Silicone-g-AG-HEP1 film showed a similar reduction of protein adsorption. Non-specific adsorption of proteins on the hydrophilic AG polymer is known to be very low, and AG and its derivatives are often used as the supporting materials for protein separation to minimize the non-specific adsorption. Thus, the observed reduction in protein adsorption on the Silicone-g-AG4 and Silicone-g-AG-HEP1 films can be attributed to the AG layer. On the other hand, the Silicone-g-HEP film is less effective in reducing protein adsorption (adsorbed BSA and FBG was reduced by ~51% and ~80%, respectively). This is because HEP is able to interact with some kinds of proteins, including BSA and FBG. Nevertheless, if the immobilized HEP is low (2.6 µg/cm²), such as on the Silicone-g-AG-HEP1 film, the protein-repellent property of AG is preserved (compared with the Silicone-g-AG4, FIG. 8).

The effect of protein adsorption on pristine silicone and Silicone-g-AG4 films on subsequent bacterial adhesion and biofilm formation was investigated using FBG and *S. aureus*. FIG. S9(a) and S9(b) show the SEM images of adherent *S. aureus* on these films after pretreatment with FBG. Increased clustering of the bacterial cells can be observed in FIG. S9(a) as compared with FIG. 4(a), which is consistent with results reported earlier that showed pre-adsorbed FBG on polypyrrole surface enhances *S. aureus* adhesion on the surface and clumping. This is attributed to the FBG binding protein (clumping factor) expressed by the *S. aureus* cells. The number of adherent bacterial cells increased slightly on the Silicone-g-AG4 film after pretreatment with FBG (comparing FIG. S9(b) with 4(b)) but these cells remained as single units rather than clusters. FIG. S9(c) and S9(d) show the SEM images of *S. aureus* biofilm on the pristine silicone and Silicone-g-AG4 films pre-treated with FBG. A thick biofilm formed on pristine silicone film regardless of whether FBG is present or not. However, the Silicone-g-AG4 film after FBG pretreatment is still able to resist biofilm formation because the extent of FBG adsorption is low (FIG. 8).

Figure 9:
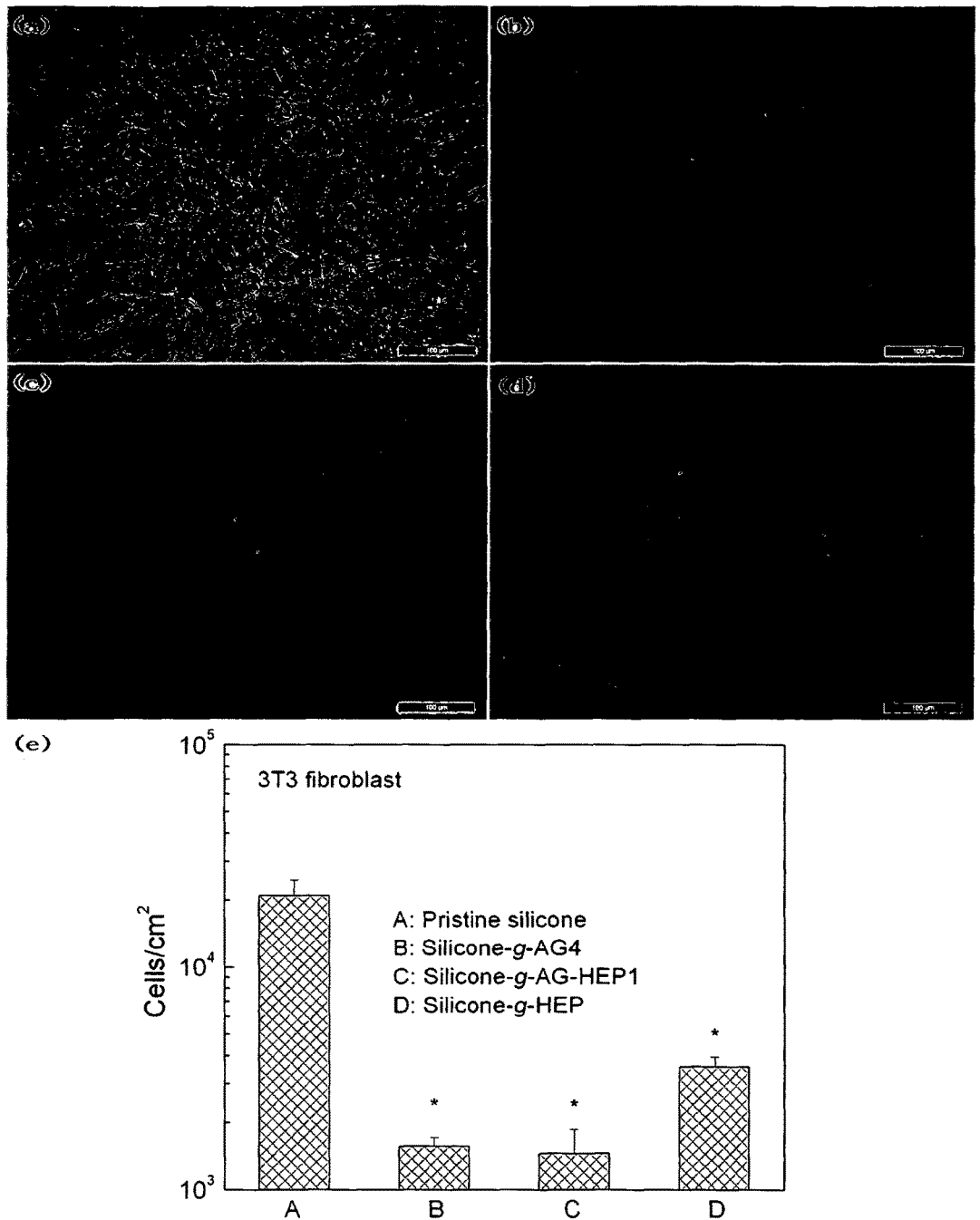
FIG. 9 Optical microscopy images of (a) pristine silicone, (b) Silicone-g-AG4, (c) Silicone-g-AG-HEP1 and (d) Silicone-g-HEP film surfaces after incubation with 3T3 fibroblasts ($2 \times 10^5$ cells/mL) for 24 h. Scale bar is 100 μm. (e) Quantitative analysis of adherent 3T3 fibroblast cells per $cm^2$ of film surface using MTT assay. * Significant differences (P<0.05) compared with pristine silicone.

In the cell adhesion assay, 3T3 mouse fibroblasts were selected as model mammalian cells to study their interaction with the modified silicone films. FIG. 9(a-c) show the optical microscopy images of the adherent 3T3 fibroblast cells on the pristine and modified silicone surfaces. A large number of 3T3 fibroblasts readily adhered on pristine silicone surface (FIG. 9(a)), while fibroblast adhesion was almost completely inhibited on the AG and AG-HEP modified surfaces (FIGS. 9(b) and 9(c)). It also can be seen from FIG. 9(d) that HEP is not as effective in preventing 3T3 fibroblast adhesion as AG and AG-HEP. The AG and AG-HEP modified silicone reduced 3T3 fibroblast adhesion by ~92% and ~93%, respectively, as compared to pristine silicone, while the reduction on the HEP modified silicone is ~83% (FIG. 9(e)). The difference in the extent of fibroblast cell adhesion on the AG, AG-HEP and HEP modified silicone films is likely related to their protein-repellent properties, as it has been reported that reduction of non-specific protein adsorption is critical in the inhibition of cellular interaction with material surface.

Although AG and HEP are known to be nontoxic, the cytotoxicity of the modified silicone films need to be tested since the as-prepared AG and AG-HEP coatings are meant for implantable devices. The cytotoxicity of the pristine and modified silicone films was evaluated with 3T3 fibroblasts using the MTT assay. The viability of 3T3 fibroblasts placed in contact with the pristine and modified films for 24 h was higher than 95% in all cases (FIG. S10). No significant difference in the cell viabilities was found as compared to that in the control experiment (without any film present), indicating that these films possess no or very low cytotoxicity. These cell viability results also confirm that the reduction of cell adhesion on the modified silicone surfaces (FIG. 9) is due to the anti-adhesive property of the polymer coatings and not because of their cytotoxicity.

3.5 Hemocompatibility Assays

Figure 10:
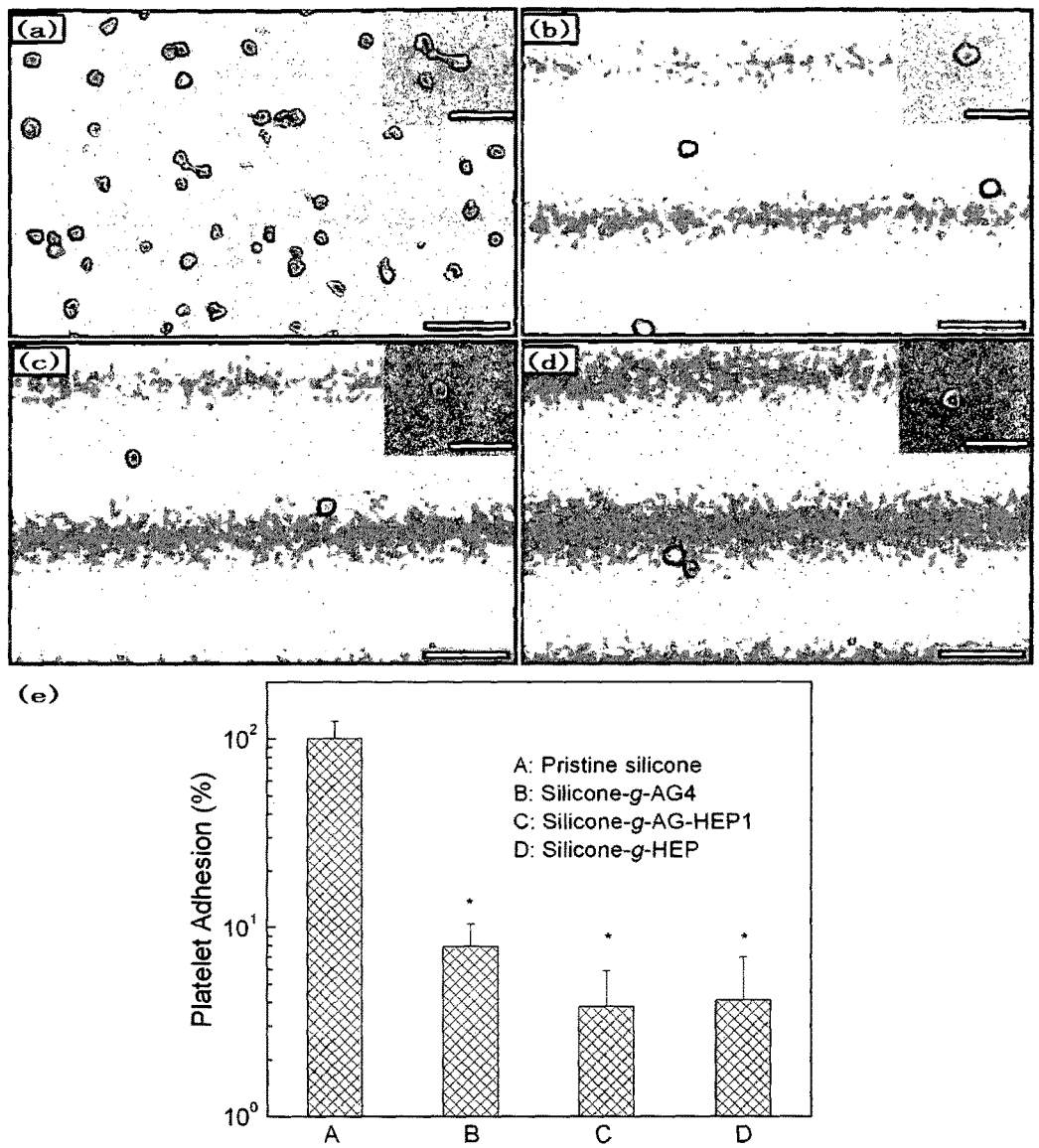
FIG. 10 SEM images of (a) pristine silicone, (b) Silicone-g-AG4, (c) Silicone-g-AG-HEP1 and (d) Silicone-g-HEP film surfaces after incubation with platelet-rich plasma for 1 h. Scale bar in (a-d) and their insets is 10 and 5 μm, respectively. (e) Platelet adhesion on the modified silicone surfaces relative to that on the pristine surface. * Significant differences (P<0.05) compared with pristine silicone.

Hemocompatibility is an important property for biomedical devices in contact with blood in human body such as central venous catheters. Platelet adhesion and activation on surfaces may induce blood clotting and thrombosis. In PD, such events can result in intraluminal obstruction and eventual outflow failure of the catheters. The blood compatibility of the AG and AG-HEP modified silicone films were evaluated from platelet adhesion and activation, hemolysis and plasma recalcification time (PRT) tests. The SEM images of platelet adhesion on pristine and modified silicone films are shown in FIG. 10(a-d). Platelets adhered readily on pristine silicone surface (FIG. 10(a)) and the adherent platelets were highly activated with the characteristics of pseudopodia and spreading. After the grafting of AG and AG-HEP on silicone, the number of adherent platelets significantly decreased (FIGS. 10(b) and 10(c)). The quantitative comparison of the number of adherent platelets on various films (FIG. 10(e)) shows that platelet adhesion on the modified silicone surface was reduced by more than 1 order of magnitude as compared to the pristine surface. The resistance to platelet adhesion on the AG and AG-HEP modified silicone films is again attributed to their protein-repellent property as discussed above since plasma protein adsorption, in particular the adsorption of platelet adhesion promoting protein, FBG, plays an important role in platelet adhesion on biomaterial surfaces. However, it should be noted that the platelets on the Silicone-g-AG4 film are still activated (inset of FIG. 10(b)), indicating that the AG coating is not effective in inhibiting the activation of platelets. On the other hand, the AG-HEP coating is effective in preventing activation of the platelets (inset of FIG. 10(c)), and this can be ascribed to the presence of HEP in the AG-HEP layer. HEP is commonly used as an anticoagulant agent and has been reported to be able to inhibit platelet adhesion and activation, which is confirmed by the low degree of platelet adhesion and activation on the Silicone-g-HEP film (FIG. 10(d)).

Figure 11:
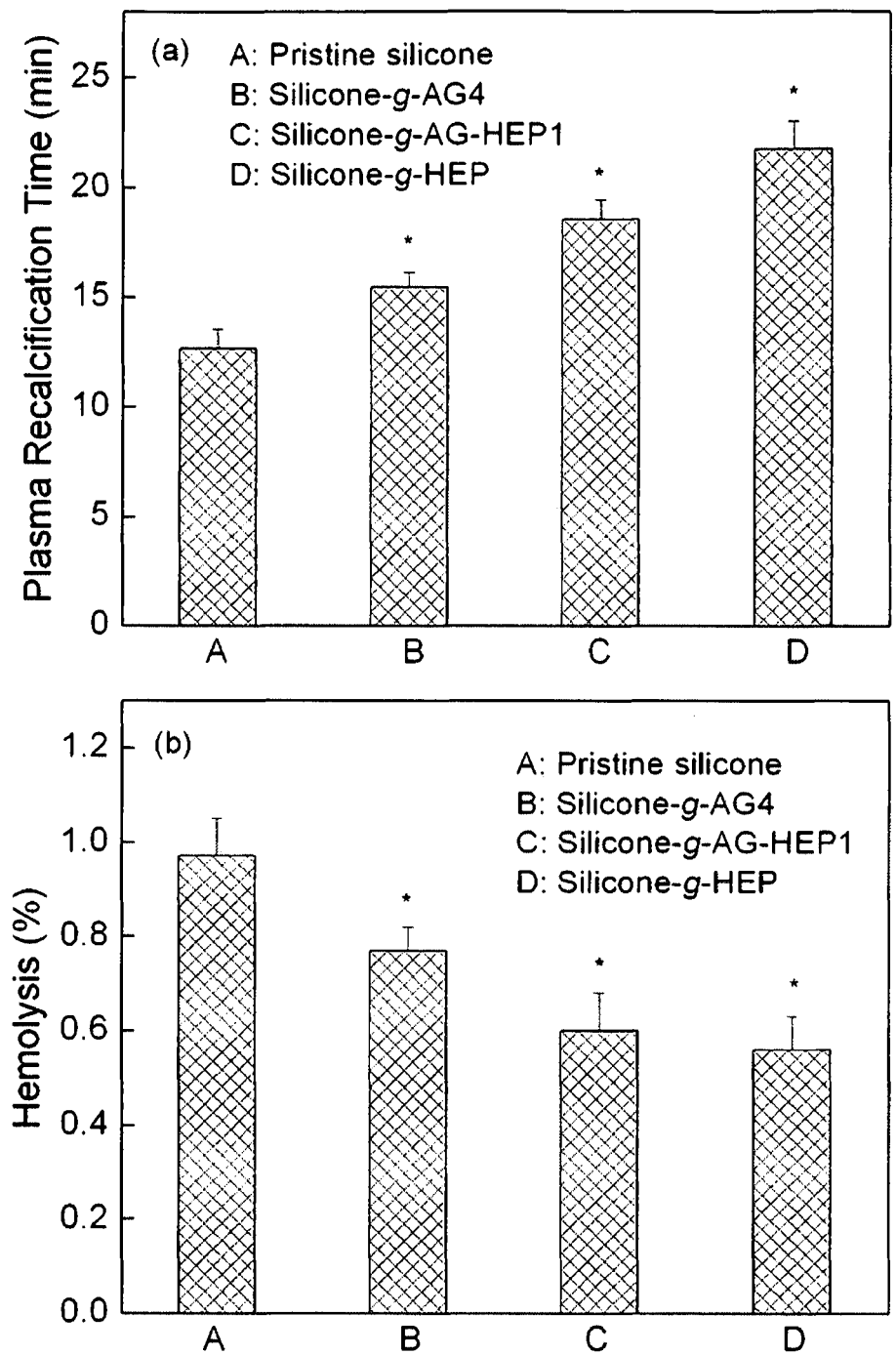
FIG. 11 (a) PRT and (b) degree of hemolysis on pristine silicone, Silicone-g-AG4, Silicone-g-AG-HEP1 and Silicone-g-HEP film surfaces. * Significant differences (P<0.05) compared with pristine silicone.
Supplementary Figures FIG. S1 XPS (a) widescan and (a') S 2p core-level spectra of pristine silicone film. The inset of (a') shows the N 1s core-level spectrum of pristine silicone.

FIG. 11(a) shows the PRT results obtained from the blood clotting tests on the pristine and modified silicone films. Grafting of AG on silicone resulted in a significant increase in PRT from ~13 to ~16 min (P<0.05), and with the presence of HEP in the AG graft layer, the PRT increased further to ~19 min. HEP is known to bind to antithrombin III (ATIII) with high affinity, resulting in a conformational change of ATIII. With this conformational change, ATIII's reactive sites are more exposed, which greatly accelerates ATIII's inhibition of the activity of blood coagulation proteases, and consequently delays the conversion of fibrinogen to fibrin and inhibits blood coagulation. Hemolysis is another issue related to the hemocompatibility of biomaterials in contact with blood. FIG. 11(b) shows the degree of hemolysis obtained with the pristine and modified silicone films. The degree of hemolysis of pristine silicone was ~1%. After the grafting of AG, AG-HEP and HEP, the modified silicone films showed significantly lower hemolysis degrees (P<0.05), ranging from 0.77% for the Silicone-g-AG4 to 0.56% for the Silicone-g-HEP film. Although according to the American Society for Testing and Materials (ASTM) F 756-00 standard, a hemolysis degree of 2% is considered nonhemolytic for biomaterials and the pristine silicone meets this requirement, the modified films further reduced the degree of hemolysis and subsequently improved the silicone's hemocompatibility.

4. Conclusion

AG and HEP polymers were covalently immobilized on medical grade biomaterials and catheter surfaces (extra-luminal and intra-luminal) to improve their antimicrobial, antifouling and hemocompatible properties. The adhesion and biofilm formation of both Gram-negative and Gram-positive bacteria were reduced by 98% and >99%, respectively, on the AG-modified surface as compared to that on pristine silicone. Biofilm formation by *C. glabrata* on the AG-modified surface was also inhibited. AG and HEP polymers grafted via similar procedures on Ti foil, polyurethane film and silicone urinary catheter surfaces were equally successful in inhibiting biofilm formation. The cross-linked AG coating of ~2 μm thickness is stable and maintains its antibacterial efficacy after 30 days aging in lysozyme solution and also after autoclaving. In addition, the AG coating can effectively resist non-specific protein adsorption, fibroblast and platelet adhesion. This is illustrated in FIGS. 8, 9 and 10, respectively. Co-immobilization of 2.6 μg/cm$^2$ of HEP in the AG coating further improves hemocompatibility by inhibiting platelet activation, prolonging PRT and reducing the degree of hemolysis. Concomitantly, the antibacterial and antifouling efficacy of AG is retained. The favorable antimicrobial, antifouling and improved hemocompatible properties as well as non-cytotoxicity of the AG-based coating offer promising opportunities for, amongst other things, combating infection and omental wrapping of PD catheters as well as reducing CABSIs and CAUTIs when using other types of catheters.

REFERENCES (1) Dell'Aquila, R.; Chiaramonte, S.; Rodighiero, M. P.; Spanó, E.; Di Loreto, P.; Kohn, C. O.; Cruz, D.; Polanco, N.; Kuang, D.; Corradi, V.; De Cal, M.; Ronco, C. Rational Choice of Peritoneal Dialysis Catheter. *Periton. Dialysis Int.* 2007, 27, S119-S125.

(2) Frant, M.; Stenstad, P.; Johnsen, H.; Dolling, K.; Rothe, U.; Schmid, R.; Liefeith, K. Anti-Infective Surfaces Based on Tetraether Lipids for Peritoneal Dialysis Catheter Systems. *Materialwiss. Werkstofftech.* 2006, 37, 538-545.

(3) Kuang, J. H.; Messersmith, P. B. Universal Surface-Initiated Polymerization of Antifouling Zwitterionic Brushes Using a Mussel-Mimetic Peptide Initiator. *Langmuir* 2012, 28, 7258-7266.

(4) Smith, R. S.; Zhang, Z.; Bouchard, M.; Li, J.; Lapp, H. S.; Brotske, G. R.; Lucchino, D. L.; Weaver, D.; Roth, L. A.; Coury, A.; Biggerstaff, J.; Sukavaneshvar, S.; Langer, R.; Loose, C. Vascular Catheters with a Nonleaching Poly-Sulfobetaine Surface Modification Reduce Thrombus Formation and Microbial Attachment. *Sci. Transl. Med.* 2012, 4, 153ra132.

(5) Benesch, J.; Tengvall, P. Blood Protein Adsorption onto Chitosan. *Biomaterials* 2002, 23, 2561-2568.

(6) Tenke, P.; Riedl, C. R.; Jones, G. L.; Williams, G. J.; Stickler, D.; Nagy, E. Bacterial Biofilm Formation on Urologic Devices and Heparin Coating as Preventive Strategy. *Int. J. Antimicrob. Agents* 2004, 23, S67-S74.

(7) Chen, X. E.; Ling, P. X.; Duan, R. S.; Zhang, T. M. Effects of Heparosan and Heparin on the Adhesion and Biofilm Formation of Several Bacteria in vitro. *Carbohydr. Polym.* 2012, 88, 1288-1292.

(8) Shanks, R. M. Q.; Donegan, N. P.; Graber, M. L.; Buckingham, S. E.; Zegans, M. E.; Cheung, A. L.; O'Toole, G. A. Heparin Stimulates *Staphylococcus aureus* Biofilm Formation. *Infect. Immun.* 2005, 73, 4596-4606.

(9) Kim, Y. D.; Dordick, J. S.; Clark, D. S. Siloxane-Based Biocatalytic Films and Paints for Use as Reactive Coatings. *Biotechnol. Bioeng.* 2001, 72, 475-482.

(10) Kim, J.; Delio, R.; Dordick, J. S. Protease-Containing Silicates as Active Antifouling Materials. *Biotechnot Prog.* 2002, 18, 551-555.

(11) Stickler, D. J.; Lear, J. C.; Morris, N. S.; Macleod, S. M.; Downer, A.; Cadd, D. H.; Feast, W. J. Observations on the Adherence of *Proteus mirabilis* onto Polymer Surfaces. *J. Appl. Microbiot* 2006, 100, 1028-1033.

(12) Rasmussen, K.; Willemsen, P. R.; Ostgaard, K. Barnacle Settlement on Hydrogels. *Biofouling* 2002, 18, 177-191.

(13) Pourjavadi, A.; Afjeh, S. S.; Seidi, F.; Salimi, H. Preparation of Acrylated Agarose-Based Hydrogels and Investigation of Their Application as Fertilizing Systems. *J. Appl. Polym. Sci.* 2011, 122, 2424-2432.

(14) Benoit, D. S. W.; Durney, A. R.; Anseth, K. S. The Effect of Heparin-Functionalized PEG Hydrogels on Three-Dimensional Human Mesenchymal Stem Cell Osteogenic Differentiation. *Biomaterials* 2007, 28, 66-77.

(15) Shi, Z. L.; Neoh, K. G.; Kang, E. T.; Wang, W. Antibacterial and Mechanical Properties of Bone Cement Impregnated with Chitosan Nanoparticles. *Biomaterials* 2006, 27, 2440-2449.

(16) Kang, I. K.; Kwon, B. K.; Lee, J. H.; Lee, H. B. Immobilization of Proteins on Poly(Methyl Methacrylate) Films. *Biomaterials* 1993, 14, 787-792.

(17) Tsai, C. C.; Chang, Y.; Sung, H. W.; Hsu, J. C.; Chen, C. N. Effects of Heparin Immobilization On the Surface Characteristics of a Biological Tissue Fixed with a Naturally Occurring Crosslinking Agent (Genipin): an in vitro Study. *Biomaterials* 2001, 22, 523-533.

(18) Hoshi, R. A.; Van Lith, R.; Jen, M. C.; Allen, J. B.; Lapidos, K. A.; Ameer, G. The Blood and Vascular Cell Compatibility of Heparin-Modified ePTFE Vascular Grafts. *Biomaterials* 2013, 34, 30-41.

(19) Kim, Y. J.; Kang, I. K.; Huh, M. W.; Yoon, S. C. Surface Characterization and in vitro Blood Compatibility of Poly(Ethylene Terephthalate) Immobilized with Insulin and/or Heparin Using Plasma Glow Discharge. Biomaterials 2000, 21, 121-130.

(20) Banerjee, I.; Pangule, R. C.; Kane, R. S. Antifouling Coatings: Recent Developments in the Design of Surfaces That Prevent Fouling by Proteins, Bacteria, and Marine Organisms. *Adv. Mater.* 2011, 23, 690-718.

(21) Pereira, A. M.; Abreu, A. C.; Simoes, M. Action of Kanamycin Against Single and Dual Species Biofilms of *Escherichia coli* and *Staphylococcus aureus*. *J. MicrobioL Res.* 2012, 2, 84-88.

(22) Nessim, S. J. Prevention of Peritoneal Dialysis-Related Infections. *Semin. Nephro.* 2011, 31, 199-212.

TABLE 1

Surface composition as determined by XPS and water contact angle of the polymer-modified silicone films

| Sample | Acrylated AG/ methacrylated HEP feed ratio (w/w %) | Reaction time (min) | [C]:[Si]:[S]:[N][a] | Water contact angle (±3°) | Heparin concentration (μg/cm$^2$) |
|---|---|---|---|---|---|
| Pristine silicone | — | — | 1:0.52:—:— | 107 | — |
| Silicone-g-AG1[b] | 100/0 | 15 | 1:0.31:—:— | 42 | — |
| Silicone-g-AG2[b] | 100/0 | 30 | 1:0.22:—:— | 35 | — |
| Silicone-g-AG3[b] | 100/0 | 60 | 1:0.15:—:— | 34 | — |
| Silicone-g-AG4[b] | 100/0 | 120 | 1:0.08:—:— | 30 | — |
| Silicone-g-AG-HEP1[c] | 90/10 | 120 | 1:0.10:0.0081:0.0036 | 29 | 2.6 ± 0.9 |
| Silicone-g-AG-HEP2[c] | 80/20 | 120 | 1:0.12:0.0090:0.0040 | 33 | 4.7 ± 0.6 |
| Silicone-g-HEP[d] | 0/100 | 120 | 1:0.14:0.015:0.0090 | 40 | 12.1 ± 1.9 |

[a][C]:[Si]:[S]:[N] molar ratio calculated from the sensitivity factor-corrected XPS C 1s, Si 2p, S 2p and N 1s core-level spectral area ratio.
[b]AG-grafted silicone prepared by UV-induced immobilization and crosslinking of acrylated AG.
[c]AG-HEP-grafted silicone prepared by UV-induced immobilization and crosslinking of acrylated AG and methacrylated HEP.
[d]HEP-grafted silicone prepared by UV-induced immobilization and crosslinking of methacrylated HEP.

The invention claimed is:

1. A medical or veterinary device comprising, on at least a part of its surface, a covalently immobilized and cross-linked agarose coating adapted to inhibit biofouling and microbial attachment, wherein said agarose is modified by the introduction of one or more of acrylate, methacrylate, (meth)acrylamide, thiol, azide, alkyne, vinylpyridine or vinylimidazole groups, or derivatives of these groups.

2. The device according to claim 1 wherein said coating is provided on a surface selected from the group comprising: a biomaterial, silicone, polyurethane and titanium.

3. The device according to claim 2 wherein said surface is a medical grade surface.

4. The device according to claim 1 wherein said coating is provided on at least a part of the device that makes contact with a patient or animal.

5. The device according to claim 1 wherein said derivatives are selected from the group consisting of: acrylic anhydride, methacrylic chloride, N-hydroxyethyl (meth)acrylamide, 1-2-carboxyethyl-4-vinylpyridinium bromide, and 1-hydroxyethyl-3-vinylimidazolium bromide.

6. The device according to claim 1 wherein said coating also comprises heparin.

7. The device according to claim 6 wherein said heparin is modified by the introduction of one or more of methacrylate, acrylate, (meth)acrylamide, silane, thiol, azide, alkyne, vinylpyridine or vinylimidazole groups, or derivatives of these groups.

8. The device according to claim 7 wherein said derivatives are selected from the group consisting of: acrylic anhydride, methacrylic chloride, N-hydroxyethyl (meth)acrylamide, 1-2-carboxyethyl-4-vinylpyridinium bromide, and 1-hydroxyethyl-3-vinylimidazolium bromide.

9. The device according to claim 1 wherein said coating is 1-10 μm thick.

10. The device according to claim 9 wherein the thickness of said coating is selected from the group consisting of 1, 2, 3, 4 and 5 μm.

11. The device according to claim 10 wherein said coating is about 2 μm thick.

12. The device according to claim 6 wherein the amount of heparin in the coating is 1-15 μg/cm$^2$.

13. The device according to claim 12 wherein the amount of heparin in the coating is selected from the group consisting of: 2.0, 2.1, 2.2, 2.3, 2.4, 2.5, 2.6, 2.7, 2.8 and 2.9 μg/cm$^2$.

14. The device according to claim 12 wherein the amount of heparin in the coating is about 2.6 μg/cm$^2$.

15. The device according to claim 1 wherein said device is a catheter.

16. The device according to claim 15 wherein said catheter is selected from the group consisting of: a peritoneal dialysis catheter, a central venous catheter and a urinary catheter.

17. A catheter having, on at least a part of its surface, a covalently immobilized and cross-linked agarose coating adapted to inhibit biofouling and microbial attachment, wherein said agarose is modified by the introduction of one or more of acrylate, methacrylate, (meth)acrylamide, thiol, azide, alkyne, vinylpyridine or vinylimidazole groups, or derivatives of these groups.

18. A catheter having, on at least a part of its surface, a covalently immobilized and cross-linked agarose and heparin coating adapted to inhibit biofouling and microbial attachment, wherein said agarose is modified by the introduction of one or more of acrylate, methacrylate, (meth)acrylamide, thiol, azide, alkyne, vinylpyridine or vinylimidazole groups, or derivatives of these groups.

19. The catheter according to claim 18 wherein the amount of heparin is about 2.6 µg/cm$^2$.

* * * * *